(12) United States Patent
McAlister

(10) Patent No.: US 8,975,458 B2
(45) Date of Patent: *Mar. 10, 2015

(54) CARBON-BASED DURABLE GOODS AND RENEWABLE FUEL FROM BIOMASS WASTE DISSOCIATION

(71) Applicant: McAlister Technologies, LLC, Phoenix, AZ (US)

(72) Inventor: Roy Edward McAlister, Phoenix, AZ (US)

(73) Assignee: McAlister Technologies, LLC, Phoenix, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/685,405

(22) Filed: Nov. 26, 2012

(65) Prior Publication Data

US 2013/0331622 A1 Dec. 12, 2013

Related U.S. Application Data

(63) Continuation of application No. 13/027,068, filed on Feb. 14, 2011, now Pat. No. 8,318,997.

(60) Provisional application No. 61/304,403, filed on Feb. 13, 2010.

(51) Int. Cl.
*C07C 1/00* (2006.01)
*C10J 3/72* (2006.01)
(Continued)

(52) U.S. Cl.
CPC .............. *C10J 3/723* (2013.01); *B01J 19/127* (2013.01); *B01J 19/1812* (2013.01); *B01J 19/20* (2013.01);

(Continued)

(58) Field of Classification Search
USPC ............ 585/240, 242; 201/7, 21, 30; 44/605, 44/606
See application file for complete search history.

(56) References Cited

U.S. PATENT DOCUMENTS

2,180,626 A 11/1939 Delorme
4,339,546 A 7/1982 Randalls
(Continued)

FOREIGN PATENT DOCUMENTS

JP 2005-289856 A 10/2005
JP 2007-314745 A 12/2007
(Continued)

OTHER PUBLICATIONS

"Geologic Sequestration of Carbon Dioxide | UIC | US EPA." US Environmental Protection Agency. Accessed: Aug. 30, 2009. <http://www.epa.gov/safewater/uic/wells_sequestration.html>. pp. 1-5.

(Continued)

*Primary Examiner* — Nina Bhat
(74) *Attorney, Agent, or Firm* — Loeb & Loeb LLP

(57) ABSTRACT

Techniques, systems, apparatus and material are disclosed for generating renewable energy from biomass waste while sequestering carbon. In one aspect, a method performed by a reactor to dissociate raw biomass waste into a renewable source energy or a carbon byproduct or both includes receiving the raw biomass waste that includes carbon, hydrogen and oxygen to be dissociated under an anaerobic reaction. Waste heat is recovered from an external heat source to heat the received raw biomass waste. The heated raw biomass waste is dissociated to produce the renewable fuel, carbon byproduct or both. The dissociating includes compacting the heated raw biomass waste, generating heat from an internal heat source, and applying the generated heat to the compacted biomass waste under pressure.

8 Claims, 16 Drawing Sheets

(51) Int. Cl.
| | |
|---|---|
| *B01J 19/12* | (2006.01) |
| *B01J 19/18* | (2006.01) |
| *B01J 19/20* | (2006.01) |
| *C01B 3/24* | (2006.01) |
| *G01N 35/00* | (2006.01) |
| *F24J 2/07* | (2006.01) |
| *C01B 3/26* | (2006.01) |
| *C10B 53/02* | (2006.01) |
| *G01M 3/22* | (2006.01) |
| *G01N 1/40* | (2006.01) |
| *G01N 1/02* | (2006.01) |

(52) U.S. Cl.
CPC ............ *C01B 3/24* (2013.01); *G01N 35/00871* (2013.01); *F24J 2/07* (2013.01); *C01B 3/26* (2013.01); *C10B 53/02* (2013.01); *G01M 3/223* (2013.01); *C10J 3/72* (2013.01); *B01J 2219/00085* (2013.01); *B01J 2219/187* (2013.01); *C01B 2203/0266* (2013.01); *C01B 2203/04* (2013.01); *C01B 2203/0465* (2013.01); *C01B 2203/0485* (2013.01); *C01B 2203/0811* (2013.01); *C01B 2203/0822* (2013.01); *C01B 2203/0872* (2013.01); *C01B 2203/0883* (2013.01); *G01N 1/405* (2013.01); *G01N 35/00613* (2013.01); *G01N 2001/021* (2013.01); *Y02B 10/20* (2013.01); *Y02E 60/366* (2013.01); *Y02E 10/41* (2013.01); *Y02E 60/364* (2013.01); *Y02E 50/14* (2013.01); *Y02E 50/32* (2013.01); *Y02T 10/16* (2013.01)
USPC .................... 585/240; 201/7; 201/21; 201/30

(56) References Cited

U.S. PATENT DOCUMENTS

| | | | | |
|---|---|---|---|---|
| 4,787,321 | A * | 11/1988 | Schnellbacher et al. | ...... 110/258 |
| 5,343,699 | A | 9/1994 | McAlister | |
| 5,882,484 | A | 3/1999 | Pyy | |
| 6,024,032 | A | 2/2000 | Sharpe | |
| 6,133,328 | A | 10/2000 | Lightner | |
| 6,155,212 | A | 12/2000 | McAlister | |
| 6,270,731 | B1 | 8/2001 | Kato et al. | |
| 6,446,597 | B1 | 9/2002 | McAlister | |
| 6,890,419 | B2 | 5/2005 | Reichman et al. | |
| 7,033,570 | B2 | 4/2006 | Weimer et al. | |
| 7,033,822 | B2 | 4/2006 | Maston | |
| 7,132,090 | B2 | 11/2006 | Dziedzic et al. | |
| 7,138,046 | B2 | 11/2006 | Roychowdhury | |
| 7,169,821 | B2 | 1/2007 | Branson | |
| 7,309,435 | B2 | 12/2007 | Rozich | |
| 7,425,315 | B2 | 9/2008 | Kruesi | |
| 7,482,078 | B2 | 1/2009 | Sridhar et al. | |
| 7,491,453 | B2 | 2/2009 | Logan et al. | |
| 7,507,341 | B2 | 3/2009 | Gallagher et al. | |
| 7,562,708 | B2 | 7/2009 | Cogliandro et al. | |
| 7,569,203 | B2 | 8/2009 | Fridman et al. | |
| 7,572,369 | B2 | 8/2009 | Gallagher et al. | |
| 7,572,530 | B2 | 8/2009 | Gottmann et al. | |
| 7,575,822 | B2 | 8/2009 | Mitlitsky et al. | |
| 7,591,880 | B2 | 9/2009 | Levan et al. | |
| 7,599,760 | B2 | 10/2009 | Dutta et al. | |
| 7,608,439 | B2 | 10/2009 | McTavish et al. | |
| 7,618,606 | B2 | 11/2009 | Fan et al. | |
| 7,628,137 | B1 | 12/2009 | McAlister | |
| 7,753,973 | B2 | 7/2010 | Galloway | |
| 7,878,131 | B2 * | 2/2011 | Becchetti et al. | ............. 110/230 |
| 7,906,559 | B2 | 3/2011 | Olah et al. | |
| 7,931,783 | B2 * | 4/2011 | Dam-Johansen et al. | ........ 201/3 |
| 7,931,997 | B2 | 4/2011 | Gottmann et al. | |
| 7,947,155 | B1 * | 5/2011 | Green et al. | ...................... 201/2 |
| 8,012,453 | B2 | 9/2011 | Saxena | |
| 8,022,260 | B2 | 9/2011 | O'Connor et al. | |
| 8,070,835 | B2 | 12/2011 | McAlister | |
| 8,071,246 | B2 | 12/2011 | Mitlitsky et al. | |
| 8,211,583 | B2 | 7/2012 | Weingaertner et al. | |
| 8,212,088 | B2 | 7/2012 | Olah et al. | |
| 8,226,798 | B2 * | 7/2012 | van Aardt et al. | .................. 201/3 |
| 8,318,997 | B2 * | 11/2012 | McAlister | ...................... 585/240 |
| 2002/0077401 | A1 | 6/2002 | Chaudhary et al. | |
| 2004/0253168 | A1 | 12/2004 | Chu | |
| 2006/0280669 | A1 * | 12/2006 | Jones | ........................ 423/445 R |
| 2007/0056842 | A1 | 3/2007 | Roychowdhury | |
| 2008/0128259 | A1 * | 6/2008 | Kostek et al. | ...................... 201/4 |
| 2008/0233029 | A1 | 9/2008 | Fan et al. | |
| 2009/0007484 | A1 | 1/2009 | Smith | |
| 2009/0183430 | A1 | 7/2009 | Schubert et al. | |
| 2009/0208784 | A1 | 8/2009 | Perry et al. | |
| 2009/0208785 | A1 | 8/2009 | McElroy | |
| 2009/0246596 | A1 | 10/2009 | Sridhar et al. | |
| 2009/0273240 | A1 | 11/2009 | Gurunathan et al. | |
| 2009/0291346 | A1 | 11/2009 | Hickey et al. | |
| 2010/0275823 | A1 * | 11/2010 | Pahls | ........................... 110/233 |
| 2010/0298450 | A1 | 11/2010 | Datta et al. | |
| 2011/0036320 | A1 | 2/2011 | Peret | |
| 2011/0070510 | A1 | 3/2011 | McAlister | |

FOREIGN PATENT DOCUMENTS

| | | |
|---|---|---|
| JP | 2010031187 A | 2/2010 |
| WO | WO-2005021474 A1 | 3/2005 |
| WO | WO-2007122498 A2 | 11/2007 |
| WO | WO-2009-002191 A2 | 12/2008 |
| WO | WO-2011031752 A2 | 3/2011 |
| WO | WO-2011100695 A2 | 8/2011 |

OTHER PUBLICATIONS

"NETL: What Is Carbon Sequestration?" US Department of Energy—National Energy Technology Laboratory. Accessed: Aug. 30, 2009. <http://www.netl.doe.gov/technologies/carbon_swq/FAQs/carbon-seq.html>.

"US EPA—Carbon Sequestration in Agriculture and Forestry: Frequently Asked Questions." US Environmental Protection Agency. Published: Oct. 19, 2006. Accessed: Aug. 30, 2009. <http://www.epa.gov/sequestration/faq.html>.

Colls, Alison. "Carbon Sequestration." Environmental Change Institute. Accessed: Aug. 30, 2009. <http://climatex.org/articles/climate-change-info/carbon-sequestration/>. pp. 1-4.

International Search Report and Written Opinion for PCT Application No. PCT/US2012/050649; Applicant McAlister Technologies, LLC; Date of Mailing: Jan. 2, 2013.

Richard, Michael Graham. "Important! Why Carbon Sequestration Won't Save Us." TreeHugger. Published: Jul. 31, 2006. <http://treehugger.com/files/2006/07/carbon_sequestration.php>. pp. 1-6.

Salleh, Anna. "Urea 'Climate Solution' May Backfire." ABC.net.au. Published: Nov. 9, 2007. Accessed: Aug. 30, 2009. <http://www.abc.net.au/science/articles/2007/11/09/2085584.htm>. pp. 1-3.

International Search Report and Written Opinion for PCT Application No. PCT/US2011/024771; Applicant: McAlister Technologies, LLC; Date of Mailing: Feb. 14, 2011; 8 pages.

Bill, Alain, Carbon Dioxide Hydrogenation to Methanol at Low Pressure and Temperature, Ecole Polytechnique Federale De Lausanne, 1998, Thesis No. 1726. p. 1-3, 9, 10, 23, 48.

* cited by examiner

CARBON-BASED DURABLE GOODS AND RENEWABLE FUEL FROM BIOMASS WASTE DISSOCIATION

CLAIM OF PRIORITY

The present application is a continuation of U.S. patent application Ser. No. 13/027,068, filed Feb. 14, 2011, now U.S. Pat. No. 8,318,997 and titled CARBON-BASED DURABLE GOODS AND RENEWABLE FUEL FROM BIOMASS WASTE DISSOCIATION, which claims priority to and the benefit of U.S. Patent Application No. 61/304,403, filed on Feb. 13, 2010 and titled FULL SPECTRUM ENERGY AND RESOURCE INDEPENDENCE, which is incorporated herein by reference in its entirety. To the extent the foregoing application and/or any other materials incorporated herein by reference conflict with the disclosure presented herein, the disclosure herein controls.

BACKGROUND

This application relates to devices, techniques and materials related to carbon sequestration and renewable energy production from biomass waste.

The Aquatic plants and vegetative groundcover, particularly farms and forests are essential carbon dioxide collectors, natural habitats for countless wildlife, and sources of fiber for applications ranging from paper products to building materials. Devastation of forests on almost all continents has occurred because of non-native pest introductions and greenhouse gas exacerbated climatic changes that have made forests vulnerable to pestilence, fire, wind, flood, and drought damages.

Throughout South, Central, and North America forest fires have destroyed vast stands of trees that have been weakened or killed by drought and disease. This represents an enormous loss of pulp and building materials. Fires and rot also produce greenhouse gases such as carbon dioxide and methane that further harm the global atmosphere. It is of paramount importance to provide practical solutions that enable rapid conversion of vegetative biomass into renewable supplies of fuels, electricity, and valuable materials before these materials are lost because of fires, decay, floods and erosion. A corollary objective is to facilitate rapid redevelopment of healthy forests, crops, and other groundcover and to facilitate production of fuel and sequestered carbon values from prescribed thinning and underbrush removal to improve forest conditions and to prevent the spread of harmful fires.

SUMMARY

Techniques, structures, apparatus and materials are disclosed for generating renewable energy, such as biofuels from biomass while sequestering carbon. Described are methods and systems for anaerobic (e.g., thermochemical) production of efficiently pressurized, refined and conveniently delivered feedstocks and products such as hydrogen, methane and carbon along with soil nutrients from biomass wastes including enormous amounts of agricultural and forest wastes.

In one aspect, a method performed by a reactor to dissociate raw biomass waste into a renewable source of energy or a carbon byproduct or both includes receiving the raw biomass waste that includes carbon, hydrogen and oxygen to be dissociated under an anaerobic reaction. Waste heat is recovered from an external heat source to heat the received raw biomass waste. The heated raw biomass waste is dissociated to produce the renewable fuel, carbon byproduct or both. The dissociating includes compacting the heated raw biomass waste, generating heat from an internal heat source, and applying the generated heat to the compacted biomass waste under pressure.

Implementations can optionally include one or more of the following features. Recovering the waste heat can include at least one of recovering heat rejected from an engine, and generating heat from a renewable energy generator include at least one of a wind energy generator, a solar energy generator, an energy generator from running water and a geothermal energy generator. The method can include advancing the compacted biomass waste towards a dissociation zone for dissociating the compacted biomass waste; and removing moisture and air from the advancing compacted biomass waste. Removing the moisture and air can include extruding the compacted biomass waste through a confined space to physically squeeze the moisture and air out. The method can include forcing the produced renewable fuel or carbon byproduct or both in a counter-flow direction from the advancing compacted biomass waste; and transferring heat from the produced renewable energy, or carbon byproduct or both that travel in the counter-flow direction. The renewable fuel can include at least one of hydrocarbon, alcohol, ammonia, and hydrogen. The carbon byproduct can include at least one of carbon dioxide, carbon monoxide and carbon. The method can include producing a durable good using the carbon produced from the biomass waste. The hydrocarbon can include at least one of methane and ethane. The alcohol can include at least one of methanol and ethanol. The method can include separating the hydrocarbon into hydrogen and carbon. Also, the method can include producing a durable good using the carbon produced from the biomass waste. The raw biomass waste can include organic material containing carbon, hydrogen and oxygen obtained in response to photosynthesis. The method can include applying a catalyst to facilitate formation of the renewable energy comprising a hydrocarbon. The catalyst can include at least one of, chromium, ceramics with rare earth constituents, a platinum metal group, nobleized nickel, and intermetallics of transition metals. The biomass waste can include at least one of glucose, lignin, and cellulosic feedstock.

In another aspect, the described methods can be implemented using a system for production of a fuel mixture from biomass waste material includes a hopper to receive raw biomass waste material to be converted to the fuel mixture comprising a hydrocarbon. A countercurrent heat exchanger is coupled to the hopper to recover waste heat from a heat source and provide the recovered heat to the hopper to heat the raw biomass waste material. A pressurized and heated reactor is coupled to the hopper to receive the heated raw biomass waste material and perform various operations. For example, the reactor includes a conveyer to apply an extrusion action to the heated raw biomass waste material to obtain a compacted biomass waste material. Also, the reactor includes a combustor to transfer heat to the compacted biomass waste material to produce the hydrocarbon containing fuel mixture using a thermochemical reaction.

Implementations can optionally include one or more of the following features. The external heat source can include a device for generating renewable energy comprising at least one of a wind energy generator, a solar energy generator, an energy generator from running water and a geothermal energy generator. The conveyer can be configured to advance the compacted biomass waste towards a dissociation zone for dissociating the compacted biomass waste; and remove moisture and air from the advancing compacted biomass waste. The conveyer can include a progressively reduced pitch of helical flights of rotating tubes on an exterior surface of the conveyer to facilitate the removal of moisture and air. The pressurized and heated reactor can be shaped to reduce a cross sectional area within the reactor for advancing the compacted biomass waste material while facilitating the removal of moisture and air. The system can include a countercurrent heat exchanger coupled to the reactor to transfer heat from the produced renewable fuel or carbon byproduct or both to the compacted biomass waste that travels in a counter-flow direction from the advancing compacted biomass waste. The renewable fuel can include at least one of hydrocarbon, alcohol, ammonia and hydrogen. The carbon byproduct can include at least one of carbon dioxide, carbon monoxide and carbon. The hydrocarbon can include at least one of methane and ethane. The alcohol can include at least one of methanol and ethanol. The system can include a hydrocarbon conversion system that includes one or more heat exchangers coupled to the reactor to receive the hydrocarbon and further coupled to the heat source to receive heat used to separate the hydrocarbon into hydrogen and carbon. The raw biomass waste can include organic material containing carbon, hydrogen and oxygen obtained in response to photosynthesis. The system can include a catalytic reaction zone for receiving a catalyst to facilitate formation of the renewable fuel comprising a hydrocarbon. The catalyst can include at least one of, chromium, ceramics with rare earth constituents, a platinum metal group, nobleized nickel, and intermetallics of transition metals. The biomass waste can include at least one of glucose, lignin, and cellulosic feedstock.

The subject matter described in this specification potentially can provide one or more of the following advantages. For example, the described techniques, systems and materials can convert biomass into energy while recycling and repurposing environmentally harmful greenhouse gases, such as carbon dioxide. Also, the described techniques, systems and material can be used to convert biomass into energy with high energy-conversion efficiency and moderate costs for capital equipment and infrastructure improvements. The described techniques also can be scaled up to tackle large biomass sources, such as forest conversion while reducing operating costs. Moreover, the described techniques can minimize or eliminate releases of carbon dioxide.

BRIEF DESCRIPTION OF THE DRAWINGS

Like reference symbols and designations in the various drawings indicate like elements.

DETAILED DESCRIPTION

Techniques, materials, apparatus and systems are described for repurposing carbon and hydrogen present in biomass waste to produce durable goods and renewable fuel. The described techniques, materials, apparatus and systems can reduce or eliminate release of harmful carbon into the environment. For example, the described techniques, apparatus, systems and materials can be used to produce carbon-based durable goods, renewable fuels, electricity, valuable chemicals, soil nutrients, and materials from organic feedstocks particularly including energy crops and wastes. The described techniques can also be used for redevelopment of forests and other vegetative groundcover that have been destroyed by disease, fire, and other harmful events.

Biomass Waste Dissociation

Figure 1:
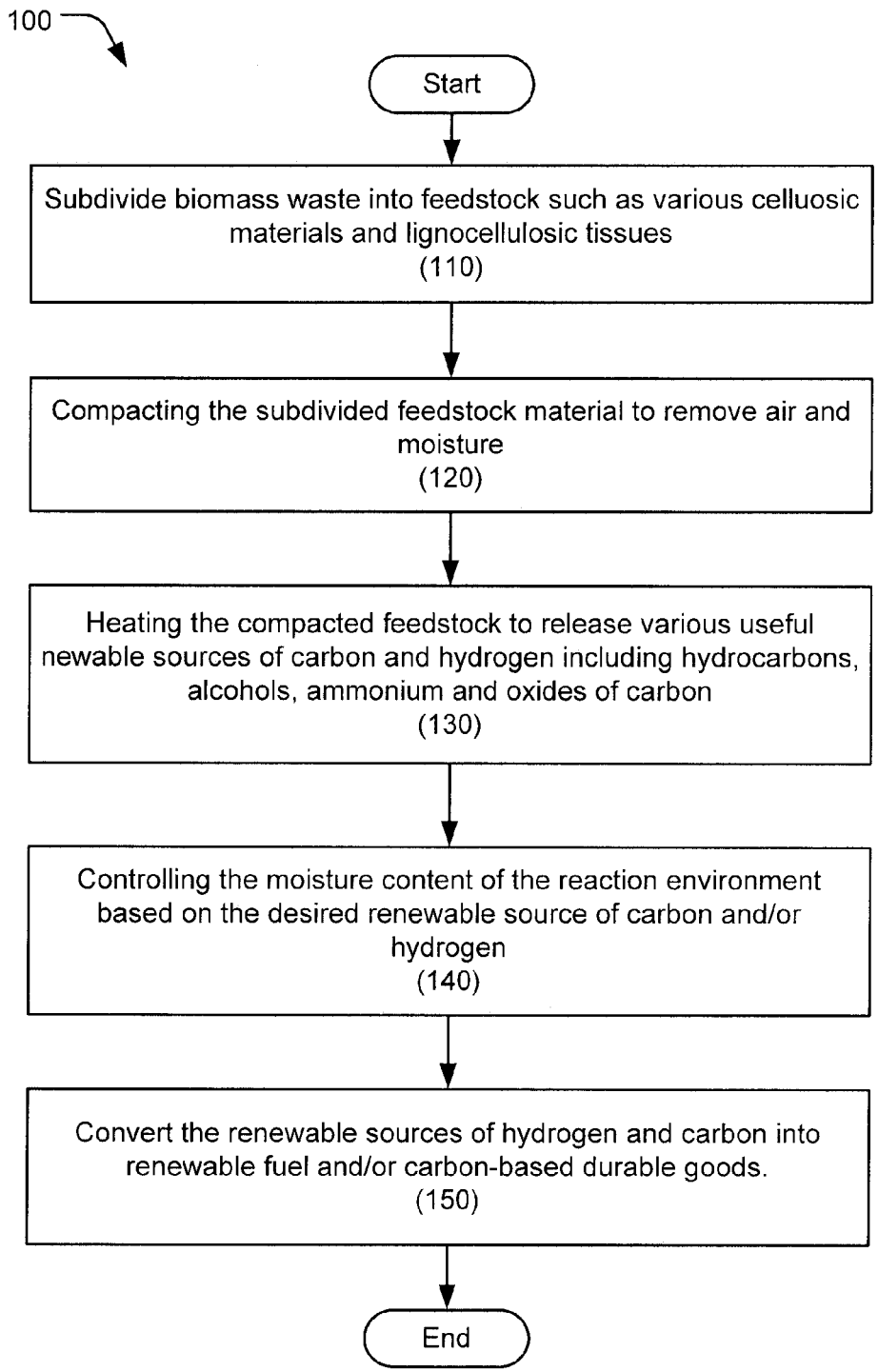
FIG. 1 shows a process flow diagram of a process for a rapid conversion of carbon, hydrogen and oxygen containing biomass wastes into useful renewable sources of carbon and hydrogen that can be used to produce carbon-based durable goods and renewable fuel.

FIG. 1 shows a process flow diagram of a process 100 for a rapid conversion of carbon, hydrogen and oxygen containing biomass wastes into useful renewable sources of carbon and hydrogen that can be used to produce carbon-based durable goods and renewable fuel.

A system (e.g., a biomass dissociation system 200 below) can subdivide the biomass waste into feedstock materials such as various cellulosic materials and lignocellulosic tissues (110). The subdivided feedstock materials can be compacted to remove air and moisture (120). The compacted biomass waste feedstock can be heated to release various useful renewable sources of carbon and/or hydrogen including hydrocarbons, alcohols, ammonium, and oxides of carbon (130). Also, the moisture content of the overall reaction environment can be controlled based on the desired renewable source of carbon and/or hydrogen (140). To control the moisture content, the compacted biomass waste feedstock that has been completely dried and de-aired can be used as a desiccant, for example. The renewable sources of hydrogen and carbon can be used to generate renewable fuel and/or carbon-based durable goods (150)

For example, as shown in Equation 1, biomass wastes can be heated sufficiently in an anaerobic environment to release desirable gases, carbon, and solid residues such as mineral oxides and other compounds. The anaerobic process for oxides of carbon and co-production of hydrogen and/or hydrocarbons from biomass wastes summarized in Equation 1 is not balanced for any particular type, amount, or ratio of lignin, cellulose, or other biomass feedstock.

$$C_xH_yO_z + HEAT \rightarrow CH_4 + H_2 + CO_2 + CO \qquad \text{Equation 1}$$

Using the process described in Equation 1, virtually any organic material can be converted in large part to hydrocarbon fuel, such as methane ($CH_4$) for distribution and storage in the existing natural gas infrastructure. Equation 2 below illustrates a general summary of the overall reactions for production of methane from typical biomass wastes such as glucose, lignin, and cellulosic feedstocks.

$$C_6H_{12}O_6 + HEAT \rightarrow 3CH_4 + 3CO_2 \qquad \text{Equation 2}$$

In some implementations, the biomass dissociation reaction can produce alcohols, such as methanol as a readily storable and transportable liquid fuel and chemical precursor. Methanol or "wood alcohol" can be extracted by heating lignocellulosic wastes through partial combustion or by anaerobic heating processes. Equations 3 and 4 summarize the output of methanol that can be achieved by selection of different anaerobic operating temperatures, pressures, and catalysts.

$$C_6H_{12}O_6 + HEAT \rightarrow 6CO + 6H_2 \qquad \text{Equation 3}$$

$$6CO + 6H_2 \rightarrow 3CH_3OH + 3CO \qquad \text{Equation 4}$$

At higher feed rates and/or lower heat release rates in a reactor, the charge does not reach the higher temperatures that produce the gases shown in Equation 1, and thus the dissociation process produces alcohol, such as methanol. Carbon monoxide can be separated from methanol by cooling the methanol vapors to form liquid methanol and to utilize the separated carbon monoxide to fuel a combustible engine, to release heat through combustion by a burner assembly, and to form hydrogen by a reaction with water as summarized in Equation 5. Hydrogen produced by the reaction summarized in Equation 5 may be used to produce methanol as shown in Equation 4, to improve operation of an engine, to improve the yield of methane and/or ethane in the biomass conversion and/or as a heating fuel.

$$CO + H_2O \rightarrow H_2 + CO_2 \qquad \text{Equation 5}$$

Figure 2:
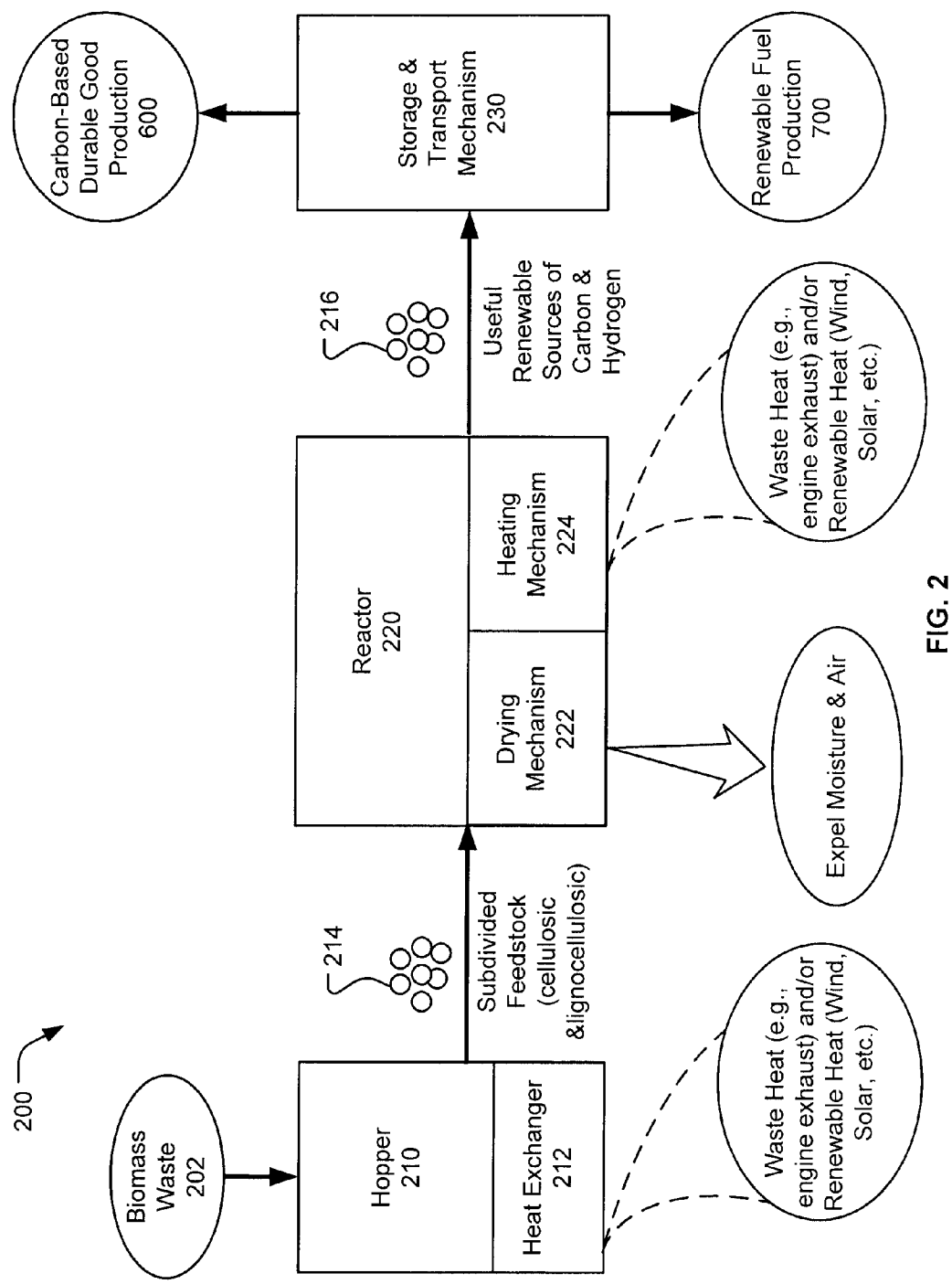
FIG. 2 shows an exemplary system for dissociating biomass waste into hydrogen and carbon carrying intermediaries.

FIG. 2 shows an exemplary system 200 for dissociating biomass waste 202 into hydrogen and carbon carrying intermediaries. The system 200 includes a biomass waste 202 intake component, such as a hopper 210 that receives the biomass waste 202 in raw form and breaks down (e.g., chips, chops, grinds, etc.) the raw material into subdivided feedstock, such as various cellulosic and lignocellulosic materials. The hopper 210 can include a heating mechanism, such as a heat exchanger 212 to pre-heat the subdivided feedstock. The heat exchanger can recapture and recycle waste heat from an external heat source (e.g., engine exhaust and/or renewable heat, such as wind, solar, running water, geothermal, etc.) or from the reactor 220.

The subdivided (and in some implementations, pre-heated) feedstock 214 is forwarded to a reactor 220 to dissociate the biomass waste feedstock 214 into useful renewable sources of carbon and hydrogen, such as various hydrocarbons, alcohols, ammonia, and oxides of carbon. The reactor can include a drying mechanism 222 to expel moisture and air from the feedstock. The drying mechanism 222 can include an extruding device to physically 'squeeze out' the moisture and air from the feedstock. Examples of the extruding device include a helical screw conveyer and a ram piston conveyer. Also, the drying mechanism 222 can include one or more heating mechanisms, such as heat exchangers that capture heat generated by the reactor 220 and recycle the captured heat to dry the feedstock. The heat exchangers can also recapture and recycle waste heat from an external heat source (e.g., engine exhaust and/or renewable heat, such as wind, solar, running water, geothermal, etc.)

The reactor 220 can also include a heating mechanism 224 for generating adequate heat used in an anaerobic reaction to dissociate the biomass waste feedstock 214 into the useful renewable sources of carbon and hydrogen 216, such as hydrocarbons, alcohols, ammonia and oxides of carbon. The generated useful renewable sources of carbon and hydrogen 216 can be forwarded to a storage and/or transport mechanism 230 to be used in additional reaction to generate renewable fuel and/or carbon-based durable goods in respective reactions as described in processes (400 and 500) and systems (600 and 700) described below. Moreover, the storage and/or transport mechanism 230 allows for efficient transport of the useful renewable sources of carbon and hydrogen 216 to remote locations for further processing.

The reactor 220 can be configured to increase thermal efficiency of the biomass waste 202 conversion process while reducing or eliminating carbon dioxide formation. For example, the reactor 220 can include mechanisms to perform various countercurrent drying (e.g., recycling heat) and elimination of air, moisture, and other oxygen donors prior to extraction of carbon, hydrocarbons such as methane, and/or hydrogen.

Figure 3:
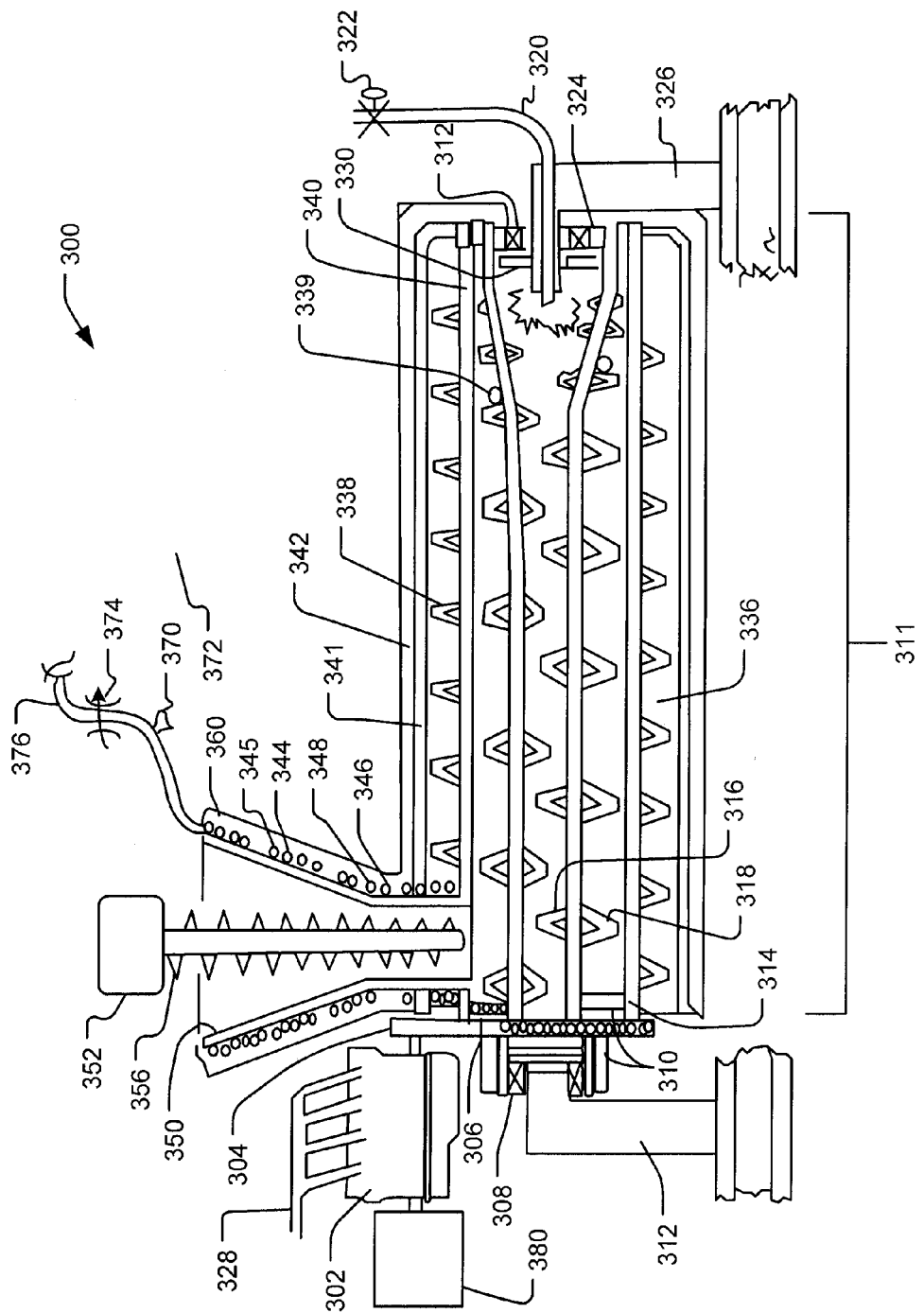
FIG. 3 shows a system for rapid conversion of biomass wastes into renewable fuel and carbon products.

FIG. 3 shows a biomass waste dissociation system 300 that uses a helical screw mechanism to expel moisture and air from the biomass waste feedstock. In operations, waste heat from an engine cooling system and/or exhaust gases can be transferred to the raw biomass materials in a hopper 350 by countercurrent turns of helical heat exchange tubing 344 and 345 that are joined to the hopper 350 at respective zones that derive the maximum amount of heat recovery from the engine 302. The heated raw biomass materials are advanced to a pressurized and heated reactor 311 for dissociation into a fuel mixture that includes hydrocarbons, hydrogen and carbon products. The heated reactor 311 includes a biomass compactor 314, such as a rotating tubular screw conveyer within a stationary containment tube 336 that compacts the raw biomass waste to a dense state and advance the compacted biomass waste towards a dissociation or reaction zone near a combustor assembly 320. The rotating tubular screw conveyer can include helical flight tubes 318 on an exterior surface of the rotating tubular screw conveyer 314 to provide an extrusion action on the compacted biomass waste.

The rotating tubular screw conveyer 314 can be driven by suitable speed reduction systems 304 and 306 through an engine 302. Based on the size of the system 300 and throughput desired, the engine 302 can may implemented as a rotary, piston, or turbine engine with an exhaust/intake valve(s) 328. The system 300 can obtain improvements in overall efficiency for generation of electricity by a suitable generator such as alternator 380 connected to the engine 302. Also, the engine 302 can be fueled by a fuel conditioning, injection, and ignition system as disclosed in a co-owned U.S. Pat. No. 6,155,212, the entire contents of which is incorporated herein by reference.

Depending on the size of the converter system 300 implemented to convert the biomass wastes to renewable energy, speed reduction components such as sprockets and a chain or a drive gear 306 and bearing support assembly 308 and 312 can be thermally isolated from the rotating tubular screw conveyer 314 by a torque-conveying thermal insulator 310. The rotating tubular screw conveyer 314 is supported similarly and thermally isolated at an opposite end by insulated bearing and support assembly 324 and 326 as shown. An insulator pack 330 provides insulation to prevent radiative and conductive heat gain by bearing 312 and other areas where protection from heat is desired.

To continuously compact the raw solid biomass materials that are entrained within the stationary tube 336, the system 300 can include a drying mechanism to remove moisture and/or air from the biomass material. The drying mechanism can include progressively reduced pitch of the helical flight tubes 318 on the exterior of the rotating tubular screw conveyer 314 and/or a reduced cross-sectional area between the rotating tubular screw conveyer 314 and the stationery tube 336. The drying mechanism can provide for expulsion of entrapped air and/or moisture from the biomass material being heated by the process by forcing the entrapped air and moisture to travel in a counterflow direction to the material being ingested through the heated hopper 350 and a feed screw 356 driven by a suitable traction motor 352 or a suitable drive train from the engine 302. Decreasing the pitch of the rotating tubular screw conveyer 314 or reducing the cross section through which compacted biomass wastes travel can further provide a compact seal to reduce or prevent leakage of gases produced by further heating of the organic materials including reactions with additions of reactive gases.

After successive expulsion of air and moisture, the compacted biomass material is dissociated into the product hydrocarbon gases as shown in Equation 1 at the dissociation or reaction zone using the heat transferred from the combustion device 320. The hot products, such as water vapor, nitrogen, oxygen, and carbon dioxide of the combustion device 320 are circulated past a spiral heat exchange tubing 316 to transfer heat to the compacted biomass materials that travel in a counterflow direction by extrusion action of the helical flight tubes 318 located on an exterior surface of the rotating tubular screw conveyer 314 as shown.

The dissociation reaction also generates a much lower volume of solid residues. The amount of solid residue can be about 2 to 10% of the original mass of organic waste. Such residues are important sources of trace minerals that can be used to revitalize soils and assure rapid growth of replacement stands of healthy forests, gardens, aquaculture, and/or other groundcover. This can expedite greenhouse gas reduction, sequestration of carbon and hydrogen, and economic development. Also, reforested areas can serve as sustainable sources of lignocelluloses for continued production of renewable methane, hydrogen and sequestered carbon.

A relatively small portion of the hydrocarbon (e.g., methane) and/or hydrogen and/or carbon monoxide generated as summarized by Equation 1 is delivered to the engine 302 and to a burner nozzle of a combustor assembly 320 through a control valve 322 as shown in FIG. 3. Sufficient amount of air is provided to assure complete combustion of fuel values that are present with minimal objectionable emissions in all applications.

The system 300 can be implemented as larger units and high through-put versions in which combustion gases from the combustor or burner assembly 320 may be circulated within tubular flights (e.g., a spiral heat exchange tubing) 316 constructed to connect through holes in the rotating tubular screw conveyer 314 with the helical flight tubes 318 to provide more rapid transfer of heat from combustor 320 to feedstock materials progressing along the outside of the helical flight tubes 318 within the containment tube 336. Gases such as methane, hydrogen and carbon dioxide that are released from heated biomass feedstocks by the thermal dissociation process are allowed to pass into an annular space between helical fins or helical flight tubes 338 and insulated tube 341 to flow in countercurrent direction to the flow of feedstock being heated by the rotating tubular screw conveyer 314. This provides for further heat conservation as heat is regeneratively added to feedstocks within the containment tube 336 that are progressively compacted and dissociated by heat transfer to enhance pressure production as shown.

Combustion gases such as water vapor, nitrogen, oxygen, and carbon dioxide reaching the hopper area 350 by travel through the interior of the rotating tubular screw conveyer 314 and/or tubular fins or helical flight tubes 316 and/or 318 enter a helical heat transfer tubing 346 to provide further countercurrent energy addition to the feedstock materials progressing through the hopper 350 as shown. Gases that are produced such as methane, hydrogen and carbon dioxide and/or carbon monoxide reaching the area of the hopper 350 by passage through holes 330 and the annular area between the tube 336 and tube 341 and/or hollow fin 338 are circulated through a tubing 348 which is wound adjacent to a helical tubing 346 for efficient countercurrent heat transfer to materials progressing to the rotating tubular screw conveyer 314 as shown. Insulation 342 and 360 prevent heat loss to the outside.

Such mixtures of product gases are provided at a suitable margin above the desired pressure by controlling the speed of rotation of the rotating tubular screw conveyer 314 and thus the compaction of solids that are delivered to the thermal dissociation stage. This provides efficient conversion of heat energy into pressure energy as desired gases are formed in substantially larger volumes than the original solid volume. In operation, a pressure sensor 370 sends pressure data to a process controller 372 for maintaining the speed of a feed conveyer 356, the rotating tubular screw conveyer 314, and the heat rate of combustor assembly 320 to achieve desired throughput, conversion temperature, and pressure of delivered product gases. A pressure regulator 374 can provide the final adjustment of product gas delivery from a regenerative converter through a pipeline 376.

The gas mixture produced by operation of the system 300 at approximately 1,000 PSI and 1025° F. (69 Atmospheres, 550° C.) can vary as shown in Table 1 with the type of biomass wastes being converted, the dwell time, and related parameters of operation. A new formulation provides for compression ignition to replace diesel fuel and includes adsorbed hydrogen in activated carbon suspensions in methanol.

TABLE 1

| Gas Product | Forest Waste | Municipal Solid Waste | Manure |
|---|---|---|---|
| Hydrogen ($H_2$) | 22 (vol %) | 33 (vol %) | 20 (vol %) |
| Methane ($CH_4$) | 60 | 53 | 61 |
| Ethane ($C_2H_6$) | 17 | 11 | 18 |
| Carbon Monoxide ($CO_2$) | 1 | 2 | 1 |

Such gas mixtures can be rapidly produced and can be supplemented with higher energy constituents such as methanol, carbon suspensions in methanol, or propane etc., to achieve virtually any desired energy content of the resulting hydrogen-combustion characterized combustion mixture in combined fuel applications. Also, the hydrogen and/or methane produced by the reaction can be redirected into the reaction zone by injection through the manifold 339 at a rate sufficient to produce the desired ratios of methane and ethane to provide pipeline quality gas or feedstocks for chemical synthesis.

With most biomass wastes, the initial output without recycling hydrogen can range from 350 to 650 BTU/scf in a lower heating value. An increased heating value can be achieved by various selections of pressure and temperature in the decomposition process or by increasing the rate that hydrogen is recycled to the reaction zone at the manifold 339.

The carbon to hydrogen ratios of the chemical species produced can be controlled by implementing a relatively extended period of operation with greatly reduced carbon production in between times that carbon is intentionally produced to aid in selling the zone before collection of desired chemical species and/or the zone after such collection. This enables carbon to be transported as a constituent of fluids that are delivered by pipeline to storage including repressurization of depleted natural gas reservoirs, to industrial plants for making carbon-enhanced durable goods, and for other purposes. A system and a method of pipeline delivery of the produced hydrocarbons, hydrogen and/or carbon products are described with respect to FIG. 15 below.

The reactions of Equations 1-5 and systems 200 and 300 above may be further improved by the use of homogeneous and heterogeneous catalysts and application of adaptive controls to improve or optimize the desired results. For example, in the reaction zone between the manifold 339 and the gas stripper ports 340, catalysts can be added to enhance hydrocarbon (e.g., methane and ethane) and alcohol (e.g., methanol and ethanol) formation by reactions that facilitate the action of hydrogen to build reactive components that synthesize to form such compounds. Examples of catalysts include chromia and other ceramics with rare earth constituents, the platinum metal group, nobelized nickel, and intermetallics of transition metals. Use of catalysts can provide an unexpected and significant reduction of equipment cost and complexity compared to conventional approaches. Similarly, lanthanide-ruthenium preparations, Fischer-Tropsch catalysts, and copper, copper intermetallics, and/or copper alloys can be used to enhance methanol synthesis from carbon monoxide and hydrogen along with production of methanol by partial oxidation of methane.

In another aspect, low cost heat can be converted into potential energy as stored energy and the utilization of such pressure to facilitate separation processes, and energy regeneration. Pressurized mixtures are separated while retaining desirable pressurization of selected gases. Such pressurized supplies of refined quality gas can be used to power engines including internal combustion engines and engines with external heat supplies.

Such energy conversion, refinement and pressurization are also utilized to deliver refined gases to distant markets by pipeline or pressurized tank cars or by liquefaction, and storage. Also, the described energy conversion, refinement and pressurization can be implemented to operate in certain areas in conjunction with one or more of the various embodiments of the U.S. Pat. No. 6,984,305, the contents of which are incorporated herein by reference.

The described systems (e.g., systems 100, 300) can provide self-reinforcing structures of tubular construction. Strengthening can be provided by helical reinforcement structures that combine heat exchange, strengthening, rigidizing, conveying, and heat resisting benefits in modular structures that can be built by rapid assembly processes. This greatly expedites deployment of the remedies needed in waste management and reduces the delivered system cost compared to conventional approaches.

Carbon-Based Durable Goods from Dissociation of Hydrocarbon and Alcohol

Figure 4:
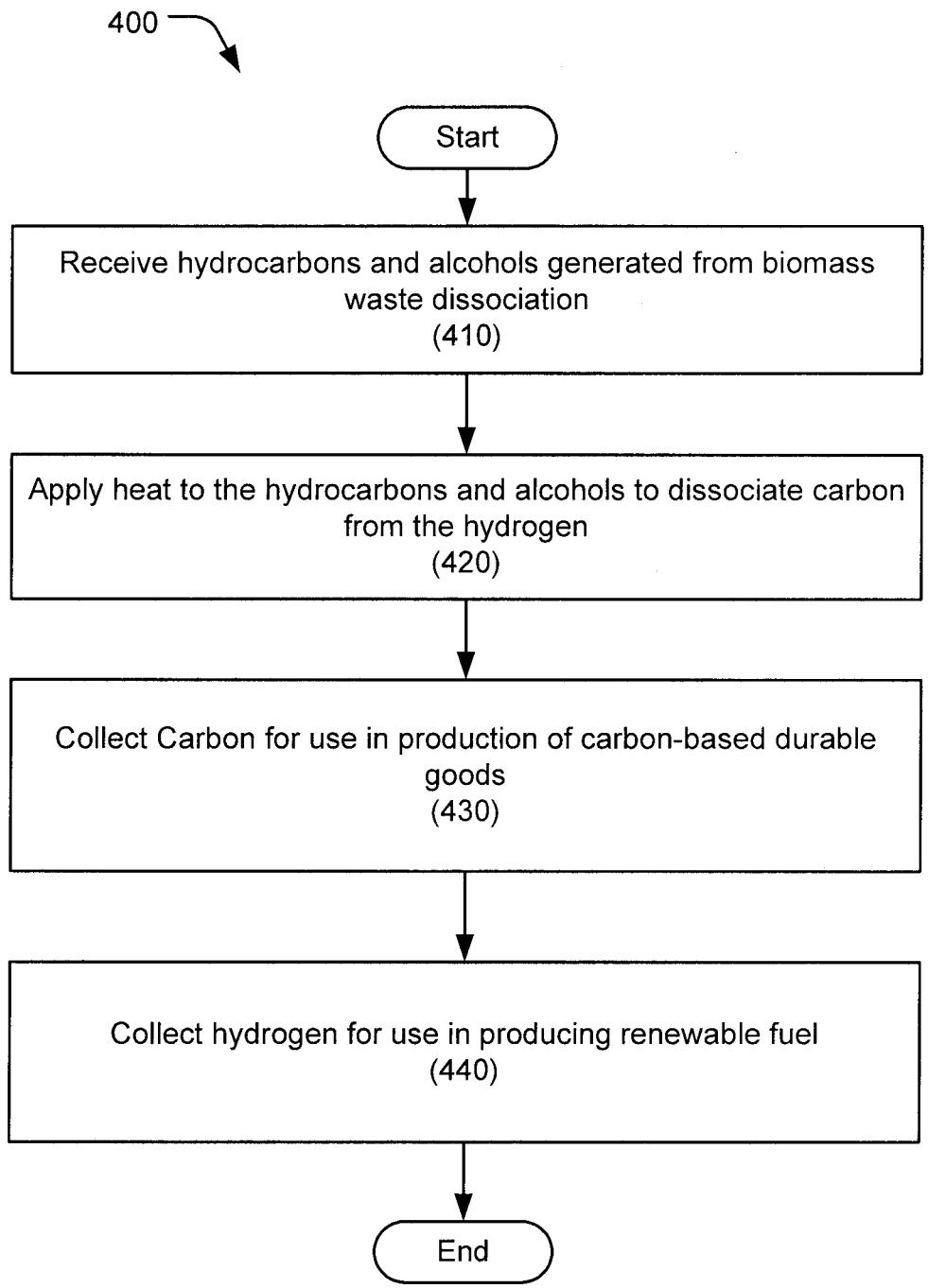
FIG. 4 is a process flow diagram of a process for dissociating hydrocarbons and alcohols to obtain carbon and hydrogen.

The hydrocarbons (e.g., methane) and alcohols (e.g., methanol) produced from biomass waste as shown with respect to process 100 and systems 200, 300 above, can be dissociated to produce carbon for a multitude of "specialized carbon" applications ranging from diamond plating and semiconductors to composite structures that are stronger than steel and lighter than aluminum. FIG. 4 is a process flow diagram of a process 400 for dissociating hydrocarbons and alcohols to obtain carbon and hydrogen. A reactor (e.g., reactor 610) can receive hydrocarbons and alcohols dissociated from biomass waste (410). The reactor can apply adequate heat and pressure to the hydrocarbons and alcohols to dissociate carbon from hydrogen (420). Equation 6 illustrates a general process of dissociating hydrocarbon fuel to obtain hydrogen and carbon. Equation 7 shows a specific reaction for dissociation of methane into carbon and hydrogen.

$$C_xH_y + HEAT_4 \rightarrow XC + 0.5YH_2 \quad \text{Equation 6}$$

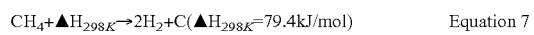

$$CH_4 + \blacktriangle H_{298K} \rightarrow 2H_2 + C (\blacktriangle H_{298K} = 79.4 \text{kJ/mol}) \quad \text{Equation 7}$$

Equation 8 shows a reaction for dissociating cellulose and fuel alcohols that contain oxygen by anaerobic decomposition to obtain carbon, carbon monoxide and hydrogen.

$$C_2H_5OH + HEAT \rightarrow C + CO + 3H_2 \quad \text{Equation 8}$$

The carbon monoxide can be reacted in an anaerobic dissociation shown in Equation 9 to increase the yield of hydrogen from feedstocks that contain carbon, hydrogen and oxygen:

$$CO + H_2O \rightarrow CO_2 + H_2 + HEAT \quad \text{Equation 9}$$

Total energy value of hydrogen and carbon monoxide produced in the endothermic reactions (e.g., Equation 1) can be 15 to 20% greater than that of methane used to source the carbon monoxide and hydrogen as shown in Equation 9.

To increase the thermochemical efficiency of the reactions, the heat used to dissociate the hydrocarbons can be harvested and recycled from engine exhaust (e.g., waste heat) or a renewable energy source, such as solar energy or heat released by combustion of a suitable fuel including products generated by reactions of Equations 1-5.

The carbon dissociated in the processes can be collected for use in the production of carbon-based durable goods (430). For example, the carbon extracted from biomass waste-produced hydrocarbons and alcohols can be used to generate carbon products including activated carbon, fibrous carbon, diamond-like coatings, graphitic components, and carbon black. These forms of carbon products can be used to manufacture durable goods, such as better equipment to harness solar, wind, moving water, and geothermal resources along with transportation components that are stronger than steel and lighter than aluminum. Recycling or repurposing carbon to produce equipment that harnesses renewable resources provides many times more energy than burning such carbon one time.

Also, the hydrogen co-produced with carbon from the dissociation of hydrocarbons and alcohols can be collected for use in producing renewable fuel (440).

Figure 5:
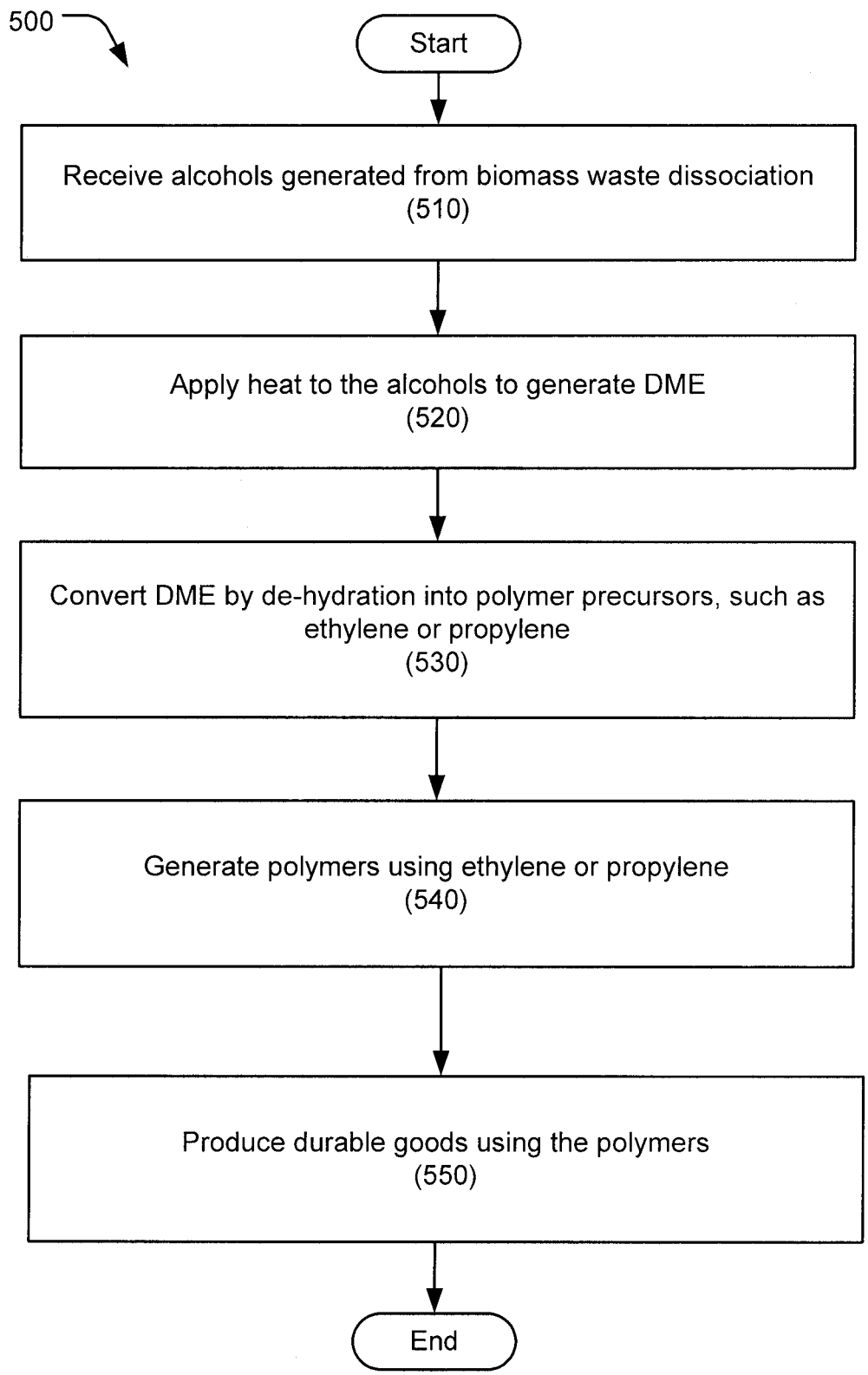
FIG. 5 shows an exemplary process for producing DME from methanol.

In some implementations, the anaerobic reaction can be modified to produce intermediate chemicals, such as Dimethalether (DME) from dissociation of the biomass waste produced alcohols (e.g., methanol). FIG. 5 shows an exemplary process 500 for producing DME from methanol. A reactor (e.g., reactor 610) can receive alcohols dissociated from biomass waste (510). The reactor can apply adequate heat and pressure to the alcohols to generate DME and water (520). Equation 10 shows a specific reaction for DME production from methanol.

$$2CH_3OH \rightarrow CH_3OCH_3 + H_2O \qquad \text{Equation 10}$$

The generated DME can be converted by de-hydration into polymer precursors, such as ethylene or propylene, which are building blocks for plastics, such as polyethylene, polypropylene and other polymers (530). Equation 11 shows a process for de-hydration of DME to obtain ethylene or propylene.

$$CH_3OCH_3 \rightarrow C_2H_4 + H_2O \qquad \text{Equation 11}$$

The above generated ethylene or propylene can be used to generate polymers (540). The polymers can be used to produce carbon-based durable goods (550). Converting methanol into polymers such as polyethylene and/or polypropylene by the processes described effectively sequesters the $CO_2$, resulting in a removal of $CO_2$ from the atmosphere.

Figure 6:
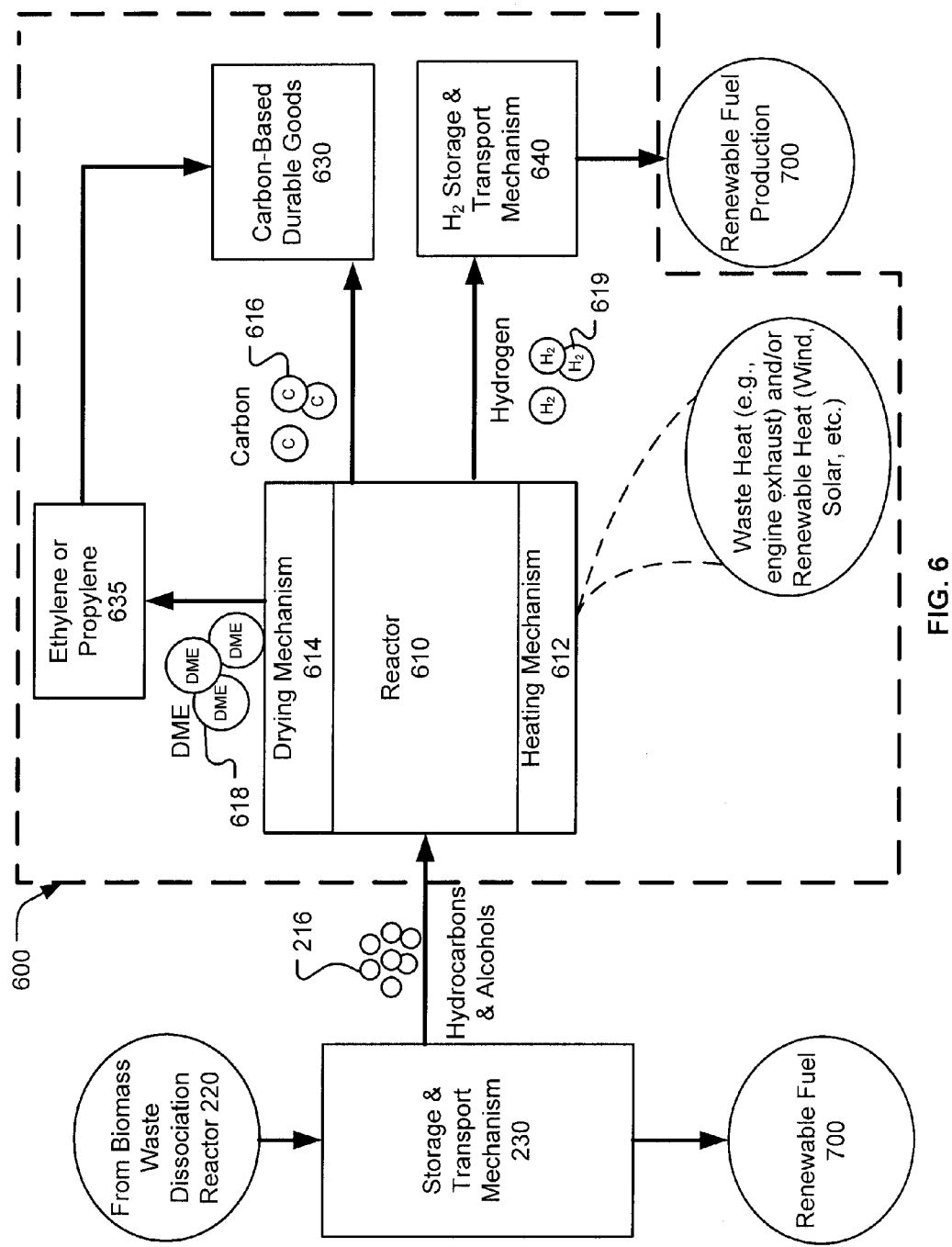
FIG. 6 is a block diagram of a system for generating carbon-based durable goods from biomass waste produced hydrocarbons and alcohols.

FIG. 6 is a block diagram of a system 600 for generating carbon-based durable goods from biomass waste produced hydrocarbons and alcohols. The system 600 includes a reactor 610 that receives the biomass waste produced hydrocarbons and alcohols 216 from the storage and transport mechanism 230 (from FIG. 2.) The reactor 610 can include a heating mechanism 612, such as heat exchangers for applying the heat used in the anaerobic reactions of Equations 6-8. The carbon 616 dissociated from the hydrocarbons and alcohols are used in production of durable goods 630.

The reactor 610 can also include a drying mechanism 614 for de-hydrating the alcohols to create DME 618, which can be used to produce ethylene or propylene 635. Also, the heating mechanism 612 can be used to dehydrate the alcohols. The produced ethylene or propylene can be used to generate polymers for producing various plastics and other carbon-based durable goods 630.

In addition, the anaerobic reaction generated in the reactor 610 produces hydrogen 619 in addition to the carbon 616 from the hydrocarbon and alcohol dissociation. The dissociated hydrogen 619 can be stored at the storage & transport mechanism 640, such as a container and/or a pipeline. Also, the hydrogen produced can be used to generate renewable fuel using a renewable fuel generating system (e.g., 700).

Separation of $CO_2$ and CO from Hydrocarbons and Hydrogen

Referring back to Equation 1, the biomass waste dissociation can produce hydrogen, oxides of carbon and hydrocarbons, such as methane.

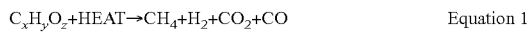

$$C_xH_yO_z + HEAT \rightarrow CH_4 + H_2 + CO_2 + CO \qquad \text{Equation 1}$$

Figure 7:
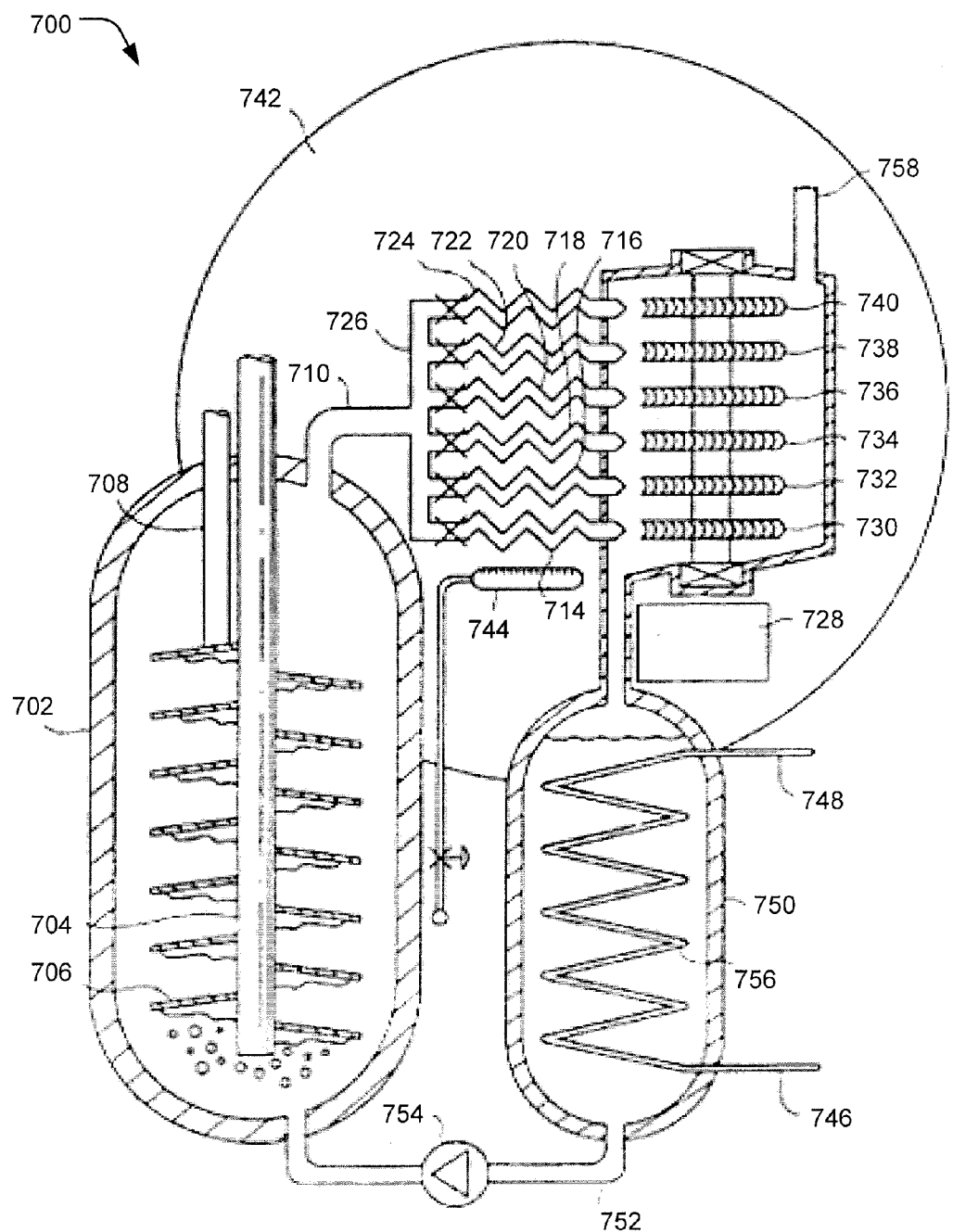
FIG. 7 shows a system for separating mixtures of product gases such as carbon dioxide and carbon monoxide from methane and/or hydrogen by pressure swing or temperature absorption.

The oxides of carbon can be separated from the hydrocarbons and hydrogen for use in separate reactions. FIG. 7 shows an exemplary system 700 for separating mixtures of product gases such as carbon dioxide and carbon monoxide from methane and/or hydrogen by pressure swing or temperature absorption. This provides for efficient separation of carbon compounds such as carbon dioxide or carbon monoxide from gases such as methane and/or hydrogen. For example, mixtures of product gases are delivered through a tube 704 and application ports 706 as shown in FIG. 7 to be exposed to water or other absorber fluid selections in a pressure vessel 702 for selective separation of carbon dioxide and/or carbon monoxide.

Methane and/or hydrogen are thus delivered to a collection tube 708 as the pressure is maintained in a pressure vessel 702. After absorption of carbon dioxide and/or carbon monoxide, the pressurized absorption fluid is delivered by a pipe 710 to a nozzle manifold 726 for delivery to heat exchangers such as 714, 716, 718, 720, 722, 724, etc. Heat from the exhaust of the engine 302 in FIG. 3 may be delivered to the heat exchangers 714, 716, 718, 720, 722, 724, etc. Additional heat can be delivered to the heat exchangers 714, 716, 718, 720, 722, 724, etc., including the heat released by a burner 744 from combustion of portions of the produced gas along with waste gases such as carbon monoxide that is released through outlet 758 by subsequent expansion of the pressurized fluid. Additional heat may also be supplied by a solar collector 742 or by resistance or induction heaters using wind or wave energy where such resources are abundant. Heated fluids are then expanded across turbines 730, 732, 734, 736, 738, 740, etc., as shown for recovery and/or conversion of energy to further improve overall efficiency.

In addition, the heated fluids can be recycled through a vessel 750 to remove heat from the heated liquid using a heat exchanger/cooling circuit 756 that circulates water or other materials through inlet and outlet ports 746 and 748 to take heat away from the heated fluid. In some implementations, the methane and/or hydrogen separated from the oxides of carbon can react with an oxygen donor circulated through the heat exchanger/cooling circuit 756 to generate water. The generated water and/or cooled fluid can pass through a port 752 and forwarded to the pressurized vessel 702 using a pump 754.

The system 700 in FIG. 7 can provide additional improvements in overall efficiency in generation of electricity by a suitable generator such as an alternator 728. Hydrogen can be used to cool these generators and reduce windage losses. After performing these functions, the same hydrogen can be then used to fuel the engine 302 or as a carbon-free fuel in combustor (e.g., burner) 744 and/or 320.

In some implementations, carbon dioxide production can be reduced or eliminated by electrolysis of derivatives of the feedstock to produce oxygen. Hydrogen gasification of such materials particularly with hydrogen and surplus carbon present can also be controlled to produce ethane in simultaneous or subsequent processes. This chemical process variation can be implemented when it is desired to rapidly convert damaged forests into pressurized supplies of methane, ethane, and hydrogen that are shipped to distant market by pipeline. Then, the pipeline can be used to continue delivery of such gases at reduced rates as a function of desired rates of forest thinning, scheduled harvesting, and maintenance programs.

Pipeline capacity established by this approach becomes an important storage system for meeting daily and seasonal variations in market demand. It is generally desired for the resultant pipeline gas to provide about 900 BTU/scf., after removal of carbon dioxide, particulates, ash, sulfur dioxide, and water as shown in FIGS. 1 and 2.

Moreover, thermal dissociation of organic substances to directly produce hydrogen and/or to produce methane for distribution and production of specialized carbon products as shown above can be far more profitable and can reduce or eliminate costly changes to existing infrastructure than conventional sequestration and storage of $CO_2$ after it has been produced by wasteful burning of organic materials. The described techniques, systems, apparatus and materials can couple carbon sequestration with production with renewable energy.

In addition to co-production by dissociation of hydrocarbon (CxHy) compounds, hydrogen can be derived by electrolytic splitting of water using any clean, alternative energy source. Hydrogen can be derived from a non-$CO_2$ producing anaerobic dissociation of organic materials and/or by utilization of energy sources such as wind, hydro, biomass, solar, tidal, geothermal, or off-peak nuclear power plants. Hydrogen can also be produced from virtually any biomass waste that ordinarily rots or burns. Also, carbon-neutral liquid compounds for storage of hydrogen can be synthesized from hydrogen and carbon dioxide.

Separation of Methanol from Carbon Monoxide

Figure 8:
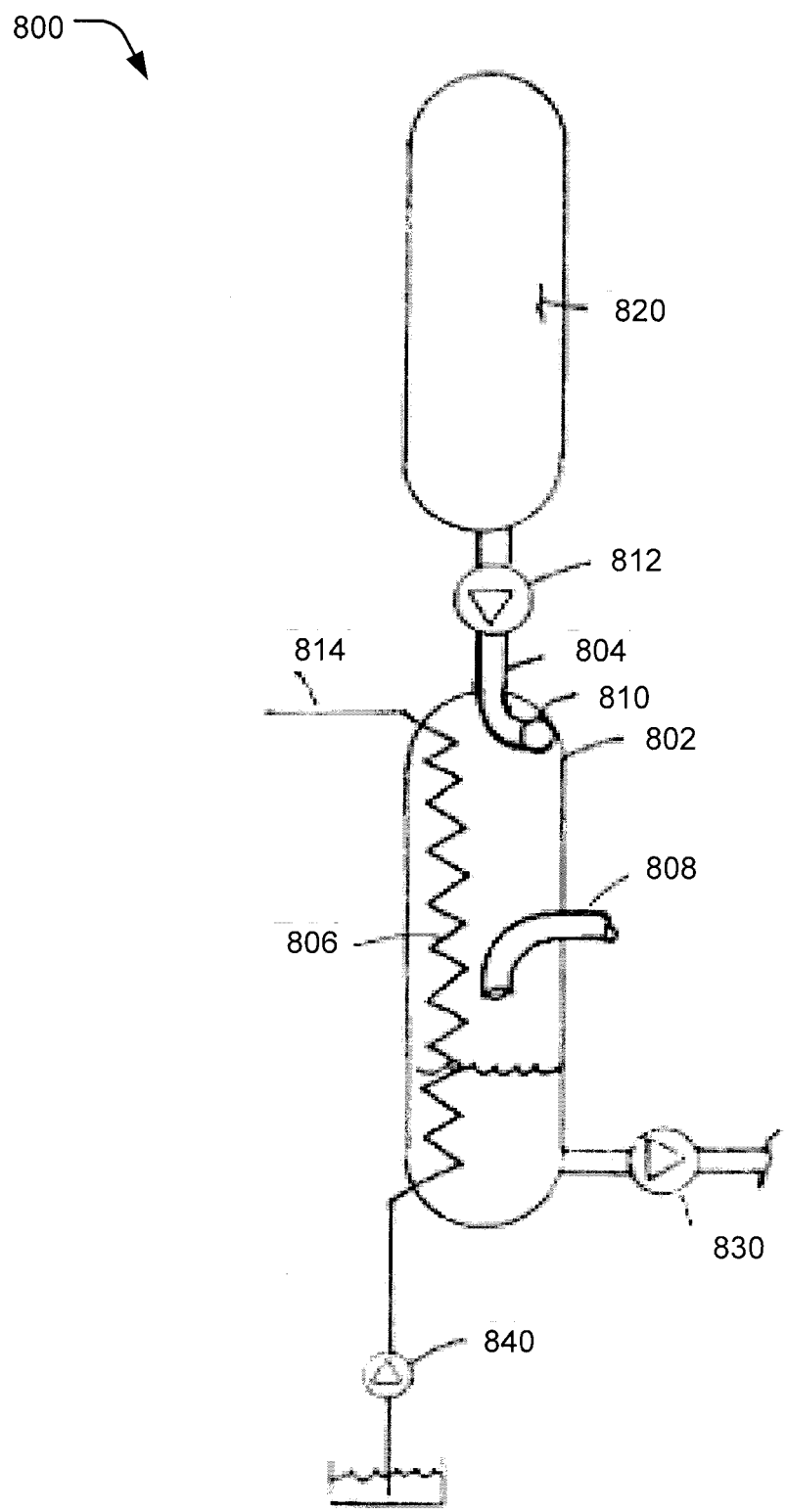
FIG. 8 is a system for separating methanol from carbon monoxide and shipment of the separated methanol to market by delivery pump.

FIG. 8 is a system 800 for separating methanol from carbon monoxide and shipment of the separated methanol to market by delivery pump 830. In operation, the system 800 performs vortex separation of denser from lighter components and provides for mixtures of carbon monoxide and methanol to enter a separator vessel or chamber 802 by a tube 804 and through a port 810 from regenerative pump/motor 812. The pump/motor 812 provides pumping action on such vapors if the delivery pressure is not adequate to achieve the delivery rate desired and provides recovery of pressure energy if the desired delivery pressure is less than the supply pressure from the system 100 of FIG. 1 or another suitable converter 820.

A heat exchange circuit 806 can be included to provide the cooling used to condense methanol. The heat exchange circuit 806, which is symbolically shown in FIG. 8, can utilize ground water or cooling tower fluid as a heat sink. The water in the heat exchange circuit 806 can be maintained at a higher pressure by a pump 840 than the vapors that enter the chamber 802, and thus any containment failure of the heat exchange circuit does not cause cooling water contamination. The cooling water that exits the separator chamber 802 from a port 814 may be used as a heated water supply or returned to the ground water system, cooling tower, or evaporation pond as appropriate for the application. After sufficiently cooling the gas mixture to create denser vapors and droplets of methanol near the walls of the chamber 802, less dense carbon monoxide is extracted by a central tube 808. Condensed methanol may be delivered by the delivery pump 830 for further processing to remove water and/or absorbed gases depending upon the purity desired.

Methanol and pipeline gas mixtures of methane, ethane, and hydrogen may be interchangeably shipped to market by the same or additional pipelines. In instances that the same pipeline is used it is preferred to changeover from one chemical type to the other by proven technologies such as the use of a pressure propelled separation slug or by pump down to clear the pipeline before refilling with the next selection to be delivered.

Biomass Conversion to Hydrocarbon Using Other Mechanisms

Other material conveyance and compaction means can be used to deliver and process biomass wastes. For example, in some implementations, a unidirectional ram delivery and compaction system can be used rather than the helical conveyer shown in FIG. 1. Other means can be implemented for processing the biomass wastes to provide the following operations: 1) compaction of the biomass wastes; 2) heat addition to eliminate air and moisture; 3) creating a plug seal of advancing material derived from the feedstock; 4) heating the advancing material to achieve the desired pressure and temperature conditions for dissociation to produce the desired chemical derivatives selected from substance options such as carbon, one or more vaporous hydrocarbons, fuel alcohols, and gases such as ethane, methane, hydrogen, and oxides of carbon; and 5) extraction of the desired chemical species in a zone that utilizes derivatives and/or remnants of the advancing material to seal or help seal the zone that provides for removal of desired chemical species. To maximize heat utilization in the resulting system, the heat added to the material advancing through such stages of progress can be obtained from countercurrent heat exchanges from the desired chemical species as it is recuperatively or regeneratively cooled. Additionally, the heat added to the material can be obtained by countercurrent heat exchanges from combustion of selected fuels.

Figure 9:
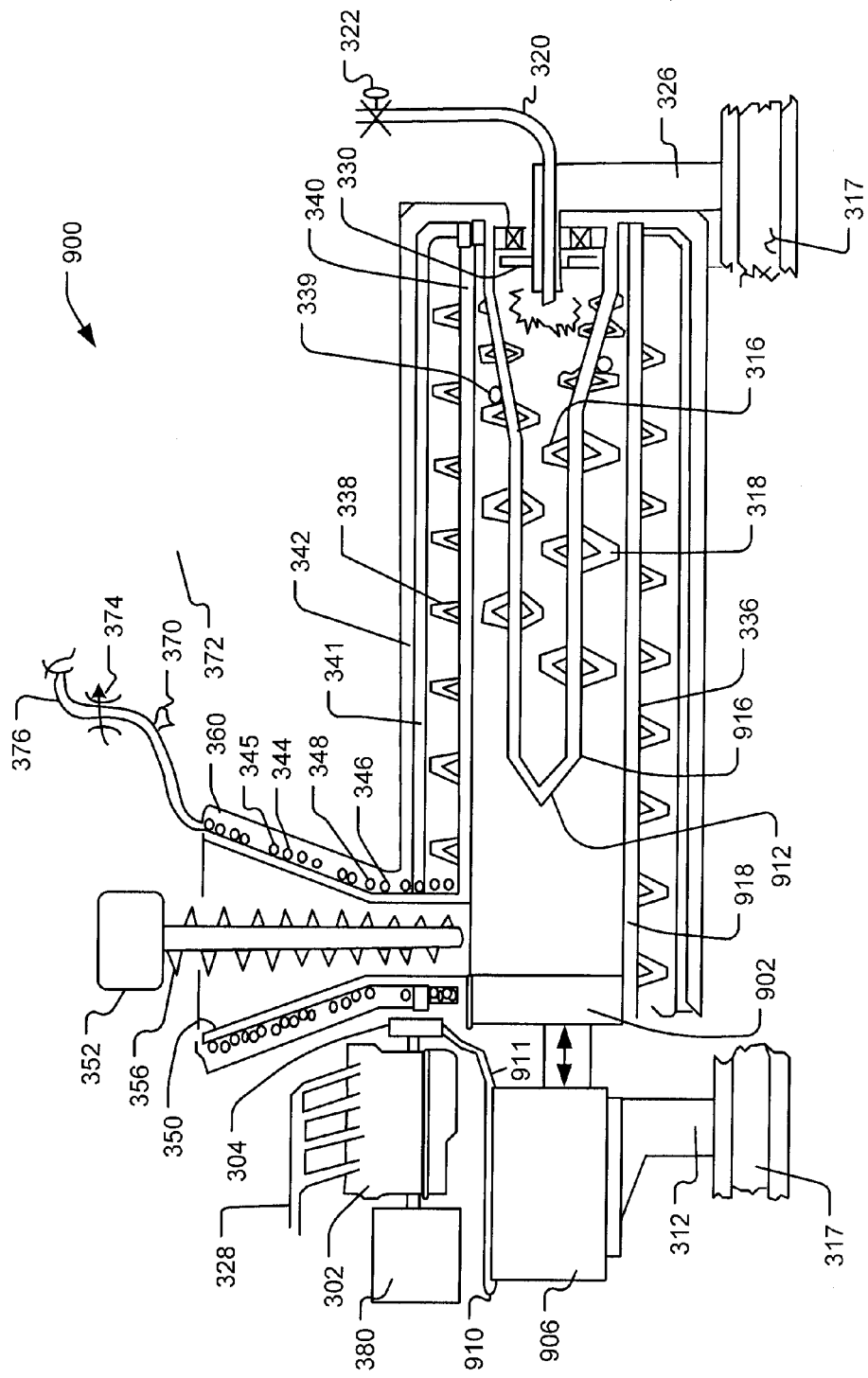
FIG. 9 illustrates another system for providing biomass waste material conveyance and compaction.

FIG. 9 illustrates an embodiment 900 similar to the system 100 of FIG. 1 that includes a ram piston compacter 902 for conversion of biomass such as sawdust, manure, and wood chips. This system 900 can operate essentially the same as the 100 of FIG. 1 except the compaction of biomass is cyclically provided by a reciprocating ram. A ram piston 902 can be forced by a hydraulic cylinder 906 to reciprocate in a stationery cylinder 918 to compact the biomass waste that has been dried and preheated by countercurrent heat exchange in the hopper 350.

The biomass waste is loaded by the conveyer 356 into a cylinder 918 when the ram piston 902 is in the position shown. The engine 302 drives a hydraulic pump 904 to deliver a pressurized working fluid through lines 910 and 911 to actuate the hydraulic cylinder 906. In the forward stroke, the ram piston 902 forces the biomass waste into a dense charge that is further compacted as it moves around a cone 912 of a heater 916 which may be stationary or rotated to enhance throughput and maintain the compaction of biomass that is progressing through the conversion process. Numerous tubes in positions typical to 339 allow expulsion of air and water vapor while further serving as a material check-valve to prevent backward flow of material that is advanced by the action of the ram piston 902. Countercurrent heat exchange from combustion gases from burner assembly 320 that travel through helical heat exchanger fins 316 and 318 raise the temperature of the biomass sufficiently to cause the dissociation reactions summarized in Equations 1, 2, 3, and 4 in response to coordination and control by controller 372.

Thus, the biomass materials can be converted into fluids such as methane, ethane, propane, methanol, ethanol, hydrogen, hydrogen sulfide, carbon monoxide, and carbon dioxide. Also, the biomass conversion as described above can produce renewable energy that can replace fossil fuels while removing objectionable levels of hydrogen sulfide, carbon monoxide, and carbon dioxide using the regenerative system 700 of FIG. 7 or by another suitable selective removal process such as pressure swing absorption, temperature swing absorption, solution absorption, and membrane separation. The renewable fuel production and carbon recycling or repurposing can be obtained using countercurrent heat exchange from sources such as combustion of a portion of one or more fuel constituents from such fluids, heat exchange from higher temperature to lower temperature substances before, during, and after production, and by heat exchange with energy conversion devices such as internal combustion engines, external combustion engines, expansive motors, and fuel cells.

Figure 10:
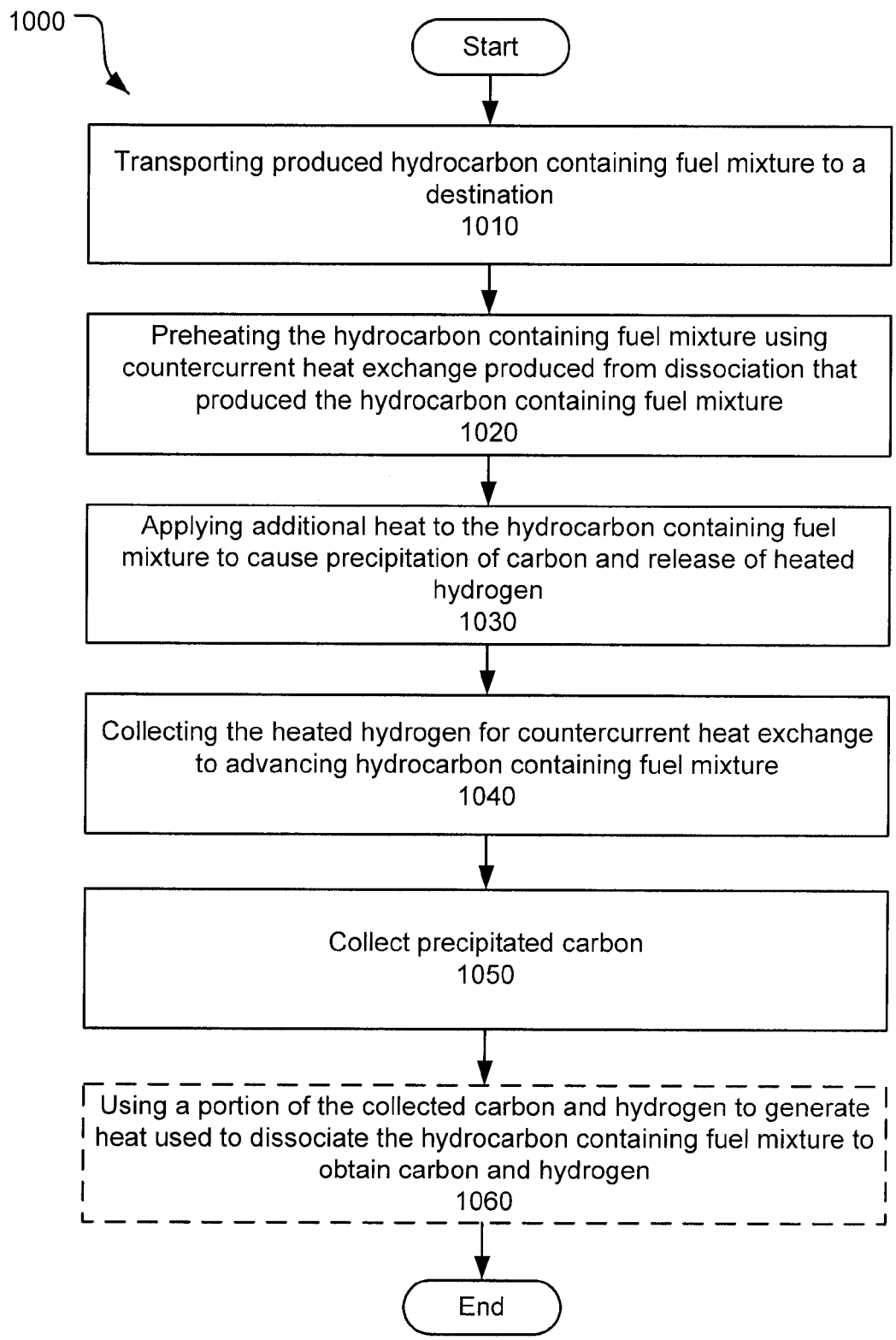
FIG. 10 is a process flow diagram showing a process for converting methane from landfills, sewage treatment plants, waste disposal operations along with other methane sources into hydrogen and carbon.

FIG. 10 is another process flow diagram showing a process 1000 for converting methane from landfills, sewage treatment plants, waste disposal operations using the systems 100, 200, 300, 700, 800 and 900 as described with respect to FIGS. 1, 2, 3, 7, 8 and 9 along with other methane sources into hydrogen and carbon as summarized in Equations 6-7 above. Hydrogen combusts seven to nine times faster compared to hydrocarbons such as gasoline, fuel alcohols, methane, and diesel fuel. This enables improved thermal efficiency in biomass conversion coupled with reduction or elimination of carbon emissions by turbine, rotary combustion, and reciprocating engine operations in which hydrogen or hydrogen-characterized fuels such as mixtures of hydrogen and methane, hydrogen and methanol, or hydrogen and carbon monoxide are injected and ignited.

Improvements in thermal efficiency gained by above described operations are particularly important for intermittent combustion engines such as rotary combustion engines and reciprocating two- or four-stroke engines such as 302 whereby direct injection and/or ignition is provided close to, at, or after top dead center to reduce or prevent heat loss and backwork during compression. This assures much greater efficiency in the conversion of fuel potential energy to work energy during the power stroke of the engine. Thus, by combusting fast burning hydrogen-characterized fuel within surplus air in the combustion chamber, considerably greater operating efficiencies can be achieved compared to engines with conventional arrangements to utilize propane, natural gas or diesel fuels.

The hydrocarbons, such as methane, produced and purified to the desired degree using the systems 100, 200, 300, 700, 800 and 900 of FIGS. 1, 2, 3, 7, 8 and 9 are transported by bulk carrier or pipeline to a suitable destination such as an industrial park (process 1010). The transported hydrocarbons are then preheated from ambient temperature to a suitable temperature such as about 1200° C. (2200° F.) by countercurrent heat exchange from hydrogen and/or carbon that is produced by dissociation (process 1020). Sufficient heat is added by radiation and/or contact with a heated substance such as graphite, iron oxide, aluminum oxide, magnesium oxide, various carbides or other ceramics to cause carbon to be precipitated on or near such heated substance selections and hydrogen is released as summarized by Equation 2 (process 1030). The heated hydrogen is collected for countercurrent heat exchange with advancing methane as described with respect to process 1020 (process 1040). Carbon that is formed by dissociation of methane is collected as a deposit or as a powder or flake material that is stripped or exfoliated from the heated substrate used in process 1030 (process 1050).

In some implementations, provided is a portion of the carbon and/or the hydrogen co-produced in the process 1030 to be combusted to heat or assist with heat addition to produce the desired pressure and temperature for dissociation of methane (1060). Alternative sources of heat addition for accomplishing dissociation of methane in process 1030 include: 1) concentrated solar energy, 2) electric induction heating of a conductive ceramic such as graphite or zirconium oxide, 3) resistance heating of such substrates and radiative heating of such substrates from a suitable incandescent source, 4) various varieties of plasma heating including plasma involving hydrogen and/or methane, 5) and/or by combustion of a suitable fuel including the methane or the products of methane dissociation such as hydrogen and or carbon.

In some implementations, the process 1000 described above can be implemented using various types of fluidized beds, helical screw or piston induced flow reactors, plasma chambers with carbon collection provisions and features, and improved carbon-black production furnaces.

Figure 11:
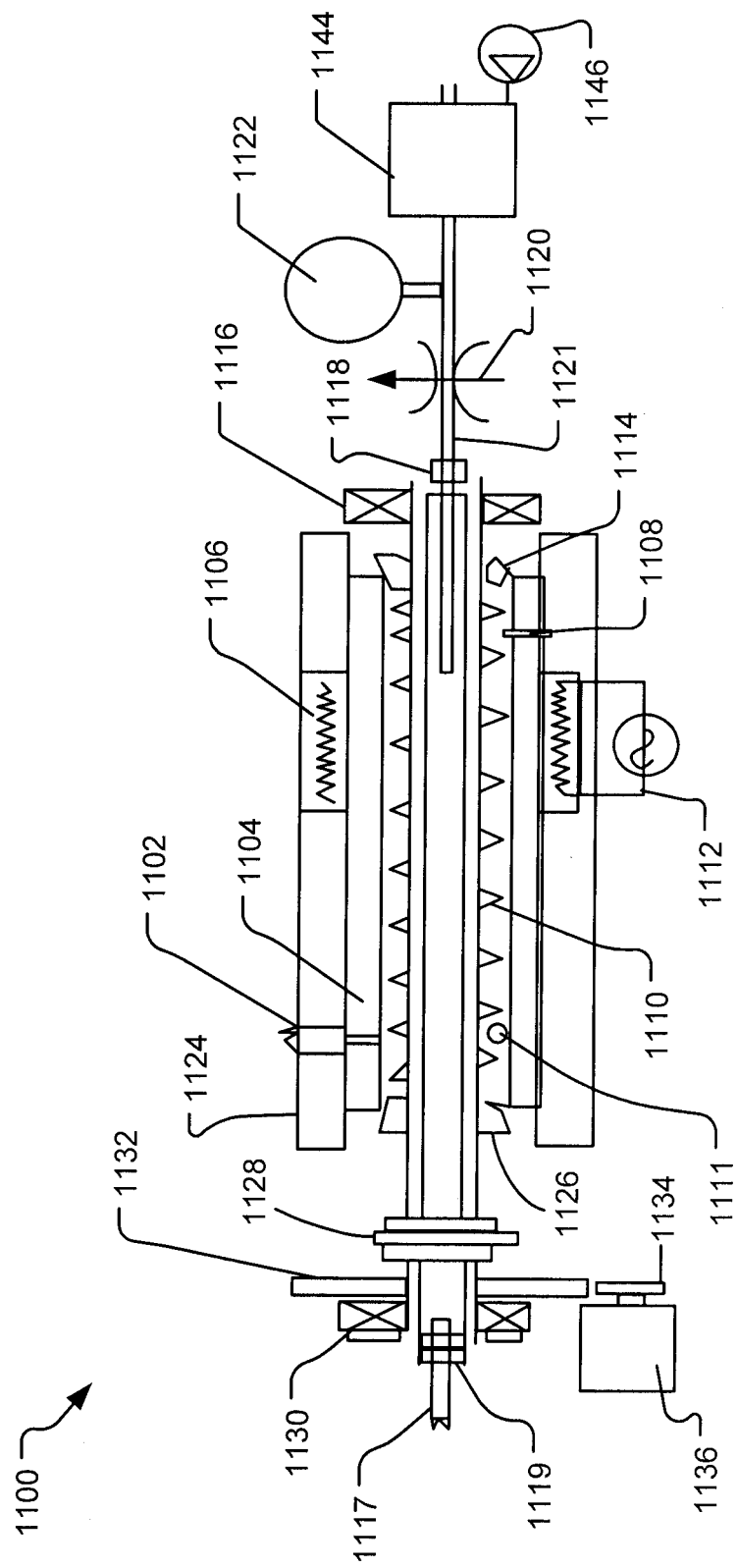
FIG. 11 is a diagram showing another efficient system for facilitating hydrogen production with carbon repurposing or recycling.

FIG. 11 is a diagram showing another efficient system 1100 for facilitating the method of hydrogen production with carbon sequestration. Similar to the above described systems and methods, the system 1100 shown in FIG. 11 can be implemented to produce hydrogen from hydrocarbons, such as methane, with much lower energy addition than required to dissociate water. Moreover, valuable forms of carbon are co-produced with hydrogen.

In operation, a hydrocarbon such as methane is delivered by a pipe 1102 to a refractory tubular barrel 1104. Within the refractory tubular barrel 1104, a refractory conveyer screw 1110 is rotated to move particles and/or substrate materials 1111 of preferred geometry and size to receive carbon that is dissociated from methane and deposited or precipitated as the methane is heated by radiation, conduction etc., according to the process summarized in Equations 6-7. Hydrogen that is co-produced is ducted through holes 1108 of a hollow helical screw conveyer 1110 to the interior bore as shown. Thus, heated hydrogen and carbon that travel towards a seal 1126 exchange heat with methane that travels toward a seal 1114. The helical screw conveyer 1110 serves as an energy exchange system for conductive and radiative heat along with performing mechanical work to rapidly accomplish the reactions summarized by Equations 6-7.

A suitable heat source 1106 is used to add heat to the system to dissociate the preheated methane. Heat may also be added by combustion of hydrogen within the hollow center of the refractory screw assembly 1110 as shown. Oxygen or another oxidant such as air can be delivered through a rotary union 1118 to be used for such combustion. Potential source for the oxygen used in hydrogen combustion can include air separation or electrolysis. Hydrogen can be delivered by a conduit 1117 through a rotary union 1119 as shown.

Based on the size of the converter system 1100, speed reduction components such as sprockets and a chain or a drive gear 1132 and a bearing support assembly 1130 can be thermally isolated from the rotating screw assembly 1110 by a torque-conveying thermal insulator assembly 1128. Similarly insulating support of bearing and rotary union 1116 assembly with the rotary union 1118 on a shaft 1121 is provided to minimize heat transfer from the helical screw assembly 1110. An insulator pack 1124 provides heat-transfer blocking to prevent radiative and conductive heat losses and other areas where protection from heat is needed.

A relatively small portion of the methane and/or hydrogen and/or carbon monoxide generated as summarized by Equations 1 and 6-7 is delivered to an engine generator assembly similar to 302 as shown in FIG. 3 to provide heat and electricity for support operations. The engine generator in FIG. 11 can include an electric drive motor 1136, an electrolyzer and/or an air separator 1144, a pump or compressor 1146, and a generator 1112 as shown. The electric motor 1136 can include a gear or sprocket drive 734 that drive the corresponding gear or sprocket drive 1132 for driving the ram piston.

The system 1100 can include a progressively reduced pitch of helical flights to continuously compact the solid biomass materials that are entrained within. In addition to the progressively reduced pitch of helical flights, the cross-sectional area between the helical rotating screw 1110 and the stationery tube barrel 1104 can be reduced in zones that serve as plug seals. This forces travel of methane in counterflow direction to carbon traveling towards extrusion through the seal 1126 and hydrogen that travels toward the rotary union 1119 within the helical rotating screw 1110 as shown.

Decreasing the pitch of the screw conveyer or reducing the cross section near or at the seals 1126 and 1114 to compact carbon particles or shapes further provides for a compact seal against the escape of hydrogen or methane. In larger applications, the helical rotating screw 1110 may be provided with slightly reversed pitch in the zone near the seal 1114 to cause compaction of carbon to produce an effective seal against methane or hydrogen loss.

An insulation system 1124 facilitates efficient countercurrent heat exchange between hydrocarbons such as methane advancing toward the seal 1114 and carbon and/or hydrogen advancing toward the seal 1126. A gear or sprocket drive 1132 is thermally isolated from the drive motor 1136, and bearings 1116 and 1130 are designed for heat isolation and/or elevated temperature service. The helical screw conveyer 1110 and barrel 1104 can be made of refractory metals or ceramic material selections such as graphite, carbides, nitrides, intermetallics, and metallic oxides.

The heat added by the heat source 1106 may be by concentrated solar energy, catalytic or flame combustion, or by electrical heating such as plasma, resistance or inductive principles preferably using renewable electricity. Oxygen produced by air separator and/or electrolyzer 1144 can be stored in an accumulator 1122 and delivered through a pressure regulator 1120. The delivered oxygen can be used when needed to provide for combustion of hydrogen and heat generation for the dissociation process such as during times that solar, wind, moving water and other renewable resources are not available or not adequate.

Photosynthesis: Organic Material for Conversion to Renewable Energy

Figure 12:
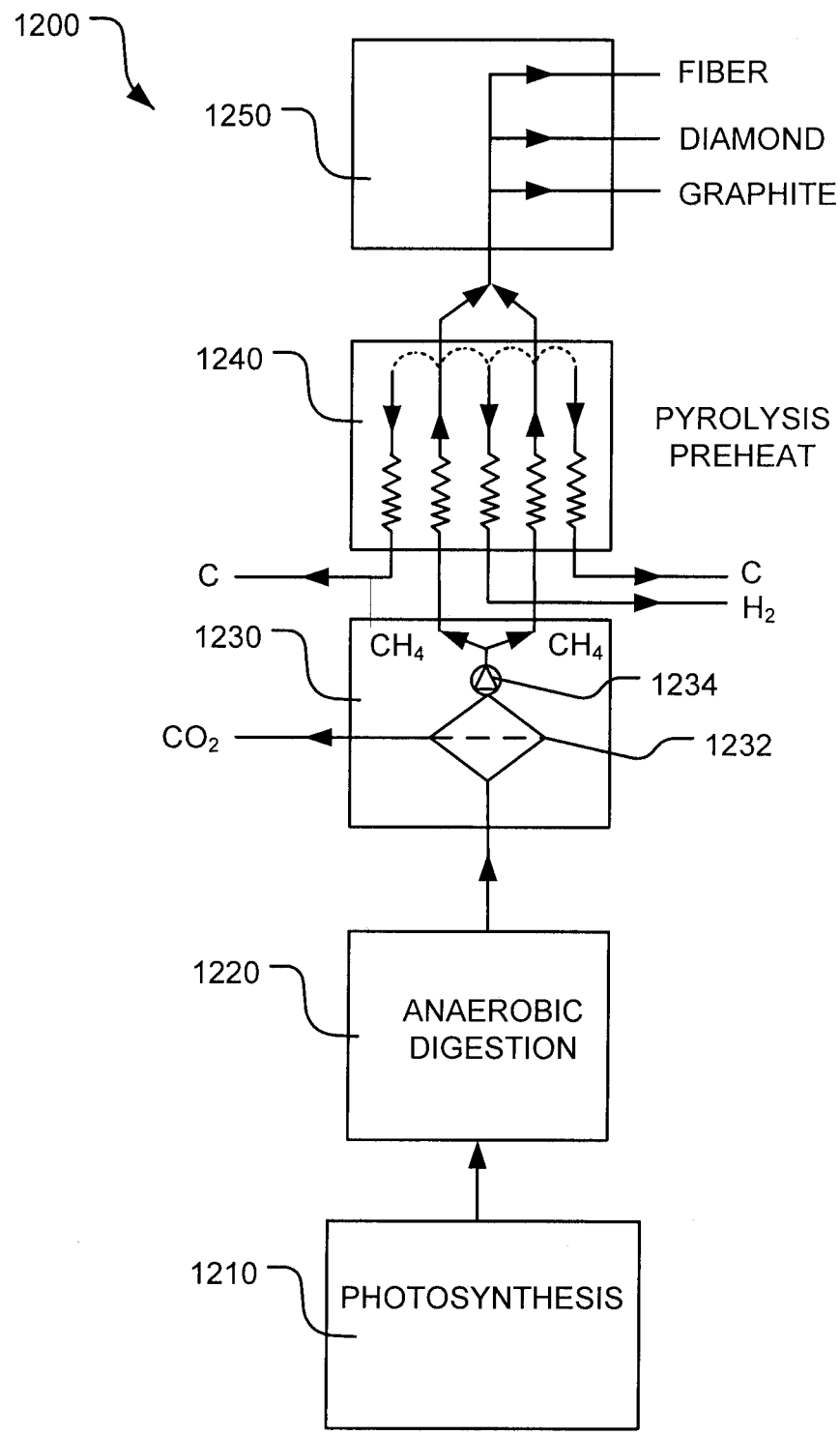
FIG. 12 is a block diagram showing an overall process for using photosynthesis to convert biomass to renewable fuel and sequester carbon.

FIG. 12 is a block diagram showing an overall process 1200 for using photosynthesis to convert biomass to renewable fuel and sequester carbon. A system (e.g., systems 100, 200, 300, 700, 800, 900 and/or 1100) can use photosynthesis to provide the organic material typically containing carbon, hydrogen, and oxygen for conversion into renewable energy (process 1210). The system uses anaerobic digestion or pyrolysis or partial oxidation to produce fuel gases such as methane and oxides of carbon (process 1220). The system separates the oxides of carbon such as carbon dioxide from the produced fuel gases (process 1230). The system can provide an appropriate filter, pressure swing adsorption, temperature swing adsorption, or selective absorption 1232 to separate methane and oxides of carbon.

The system preheats the hydrocarbons (e.g., methane) by countercurrent heat exchanges with hydrogen and carbon prior to final heat addition for dissociation as shown (process 1240). Based on the pressure of the purified fuel gases and the desired pressure for the foregoing preheat process 1240, the system can include a pressurizer 1234 to perform one or more of the following: 1) electrolysis pressurization, 2) mechanical pump or compressor operation, or 3) pressurizing release from adsorptive and/or metal hydride systems. Subsequent provisions for heat addition are selected to specialize products made from carbon derived from preheated methane as shown (process 1250).

Figure 13:
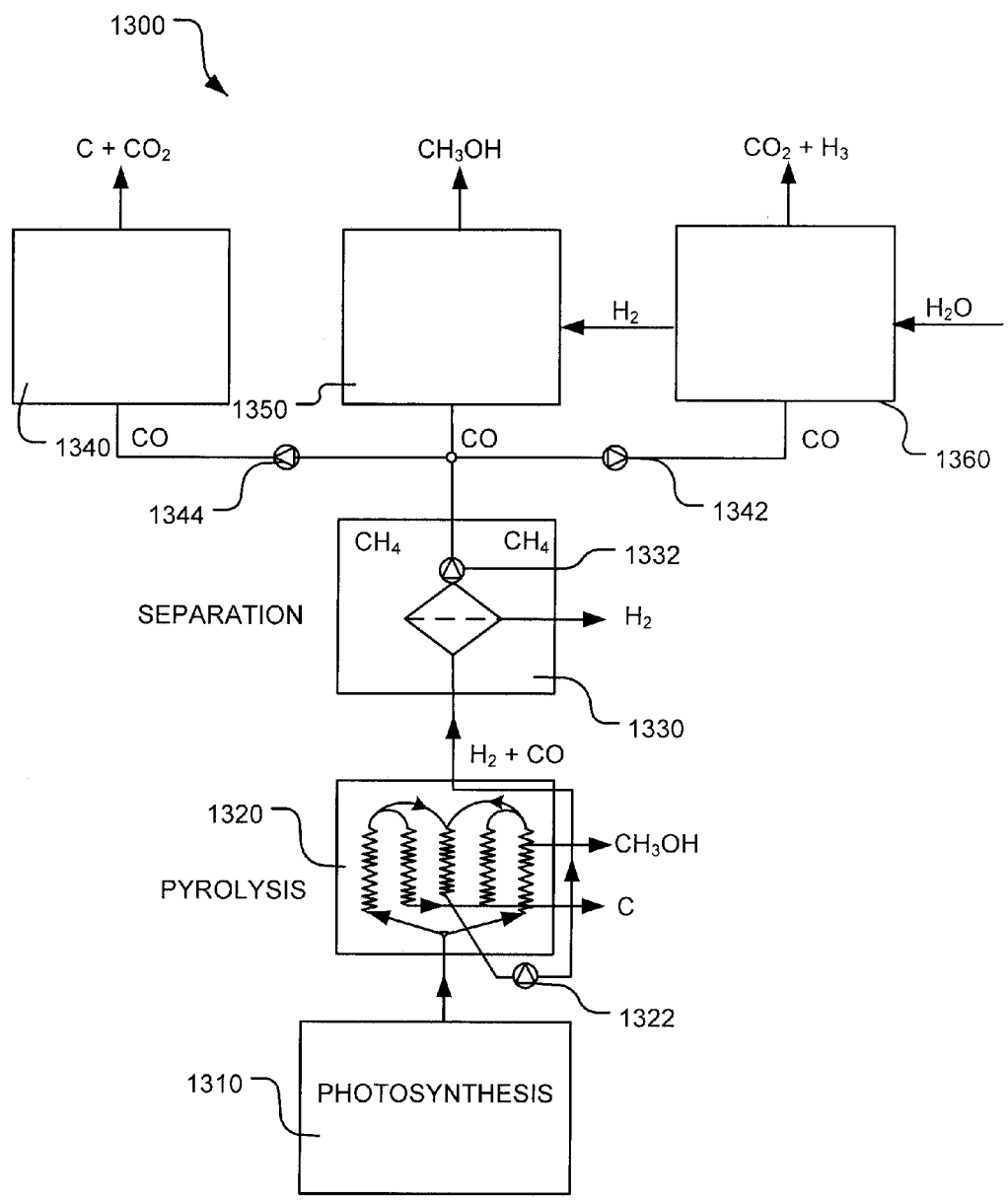
FIG. 13 is a block diagram showing another process for using photosynthesis to initiate production of valuable fuels, solvents, chemical precursors, and a wide variety of sequestered carbon products from biomass.

FIG. 13 is a block diagram showing another process 1300 for using photosynthesis to initiate production of valuable fuels, solvents, chemical precursors, and a wide variety of sequestered carbon products from biomass. Using photosynthesis, a system (e.g., system 100, 200, 300, 700, 800, 900 and/or 1100) generates organic feedstocks or biomass, such as manure, garbage and sewage (process 1310). The system converts the produced biomass by countercurrent regenerative preheating and anaerobic pyrolysis to carbon rich residue and fluids such as methanol, hydrogen, and carbon monoxide (process 1320). Biomass conversion is described above with respect to systems and methods 100, 200, 300, 700, 800, 900 and/or 1100 described with respect to FIGS. 1-3, 7-9 and 11 above.

The system delivers the gases such as hydrogen and carbon monoxide produced by anaerobic pyrolysis using a pump 1322 and separated to produce the desired degree of purification (process 1330). The system can include a pump 1332 to deliver carbon monoxide to be appropriately proportioned by metering pumps 1342 and 1344. The system can convert the delivered carbon monoxide into a wide variety of products (processes 1340, 1350 and 1360).

For example, heat can be produced as carbon monoxide dissociates into carbon and carbon dioxide (process 1340). Also, heat can be released as carbon monoxide is combined with hydrogen to produce methanol ($CH_3OH$) (process 1350). Additionally, steam can be reacted with carbon monoxide in an exothermic reaction to produce hydrogen ($H_2$) and carbon dioxide ($CO_2$) (process 1360). Heat released by these exothermic processes can be utilized to produce steam used in process 1360, to dry biomass feedstocks before additional heat is provided in process 1320, for heating anaerobic digester 1120 in FIG. 11 to increase the rate of methane and/or hydrogen production, in process 1140, and for many other useful purposes.

Solar Concentrator: Heat Source for Biomass Conversion

Figure 14A:
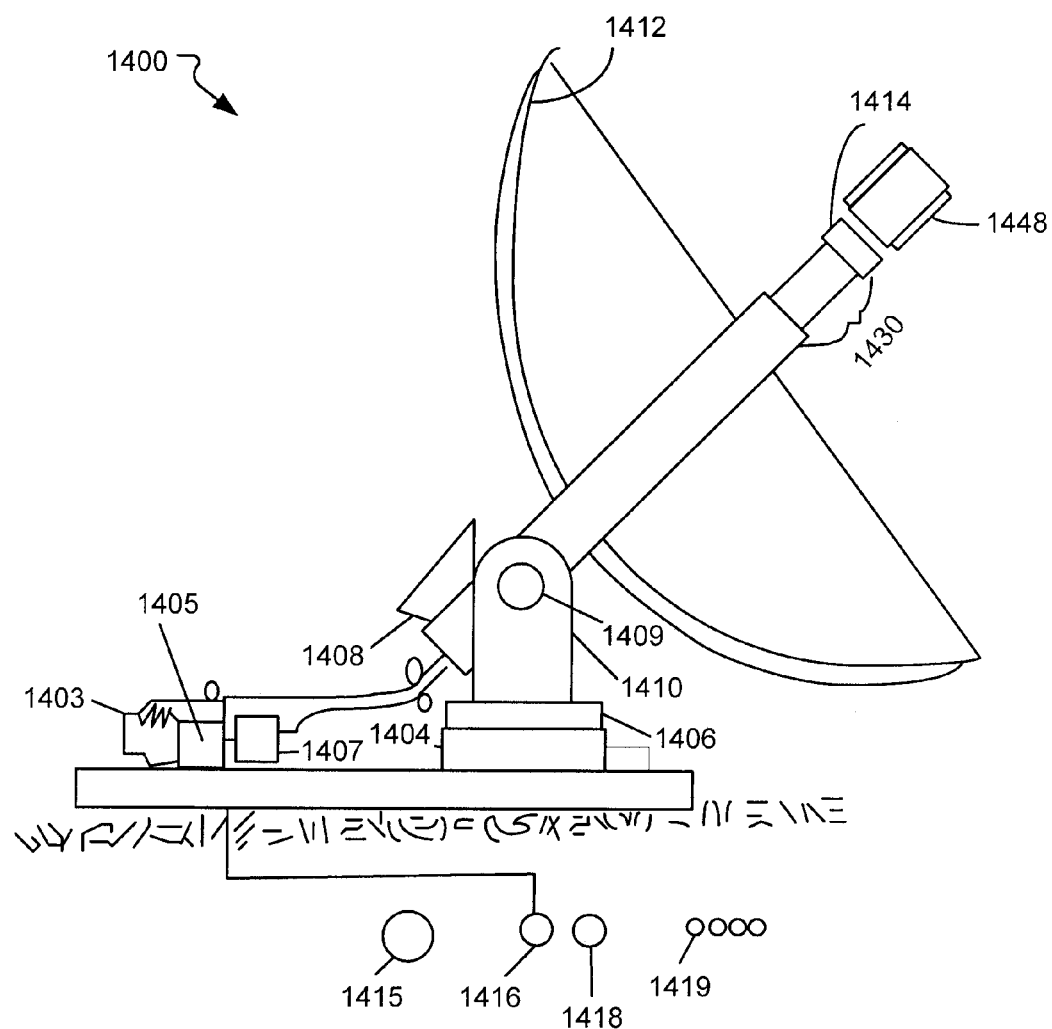
FIGS. 14A and 14B are diagrams showing a solar concentrator for using solar energy to provide heat to the biomass conversion process.
Figure 14B:
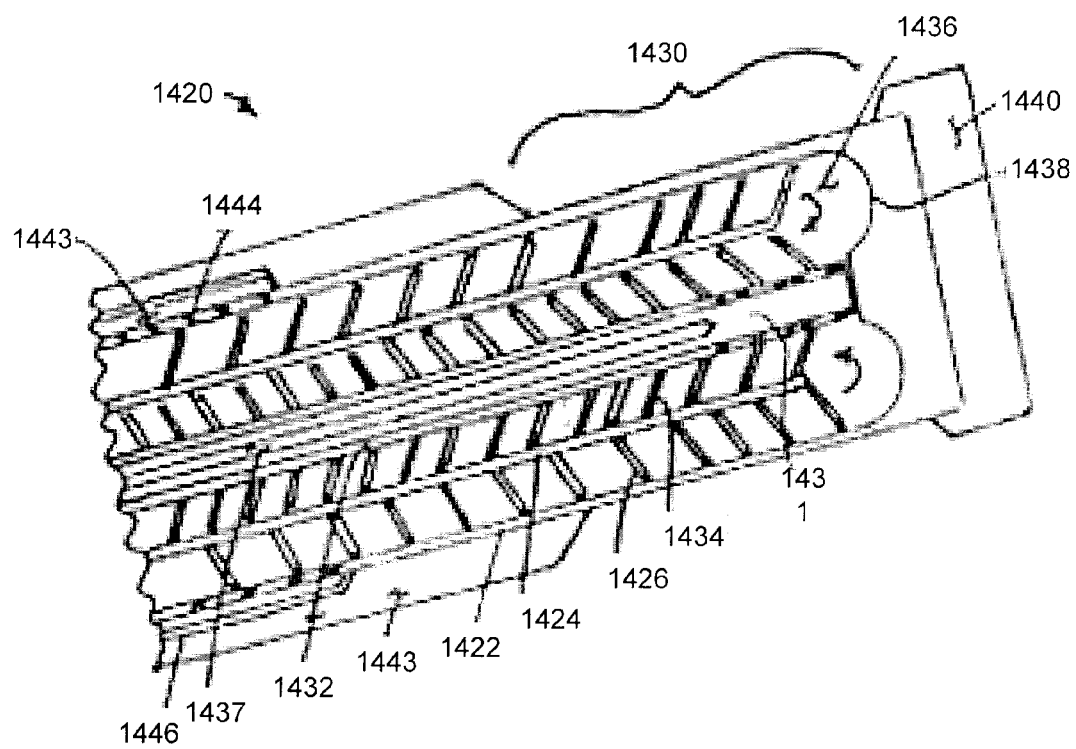

FIGS. 14A and 14B are diagrams showing a solar concentrator 1400 for using solar energy to provide heat to the biomass conversion process. The solar concentrator 1400 tracks the sun to continuously focus the reflected solar energy received by a mirror 1412 on a receiver zone 1430 of a reactor 1414 to produce a high operating temperature. Sufficient concentration of solar energy is readily achieved by the parabolic, spherical, or arrayed heliostatic mirror 1412 to produce typical operating temperatures of 500° C. to 2500° C. as facilitated by the physical and chemical properties provided by the material and configuration specifications of a containment or receiver tube 1422 in the reactor 1414. Along with the stationary receiver tube 1422, the reactor 1414 includes a rotary screw conveyer and extruder tube 1424 with integral helical screw flights 1426 that force reactive ingredients such as organic material into the reaction zone 1430. The organic material in the zone 1430 is rapidly heated to the high temperature by concentrated solar energy.

Figure 15:
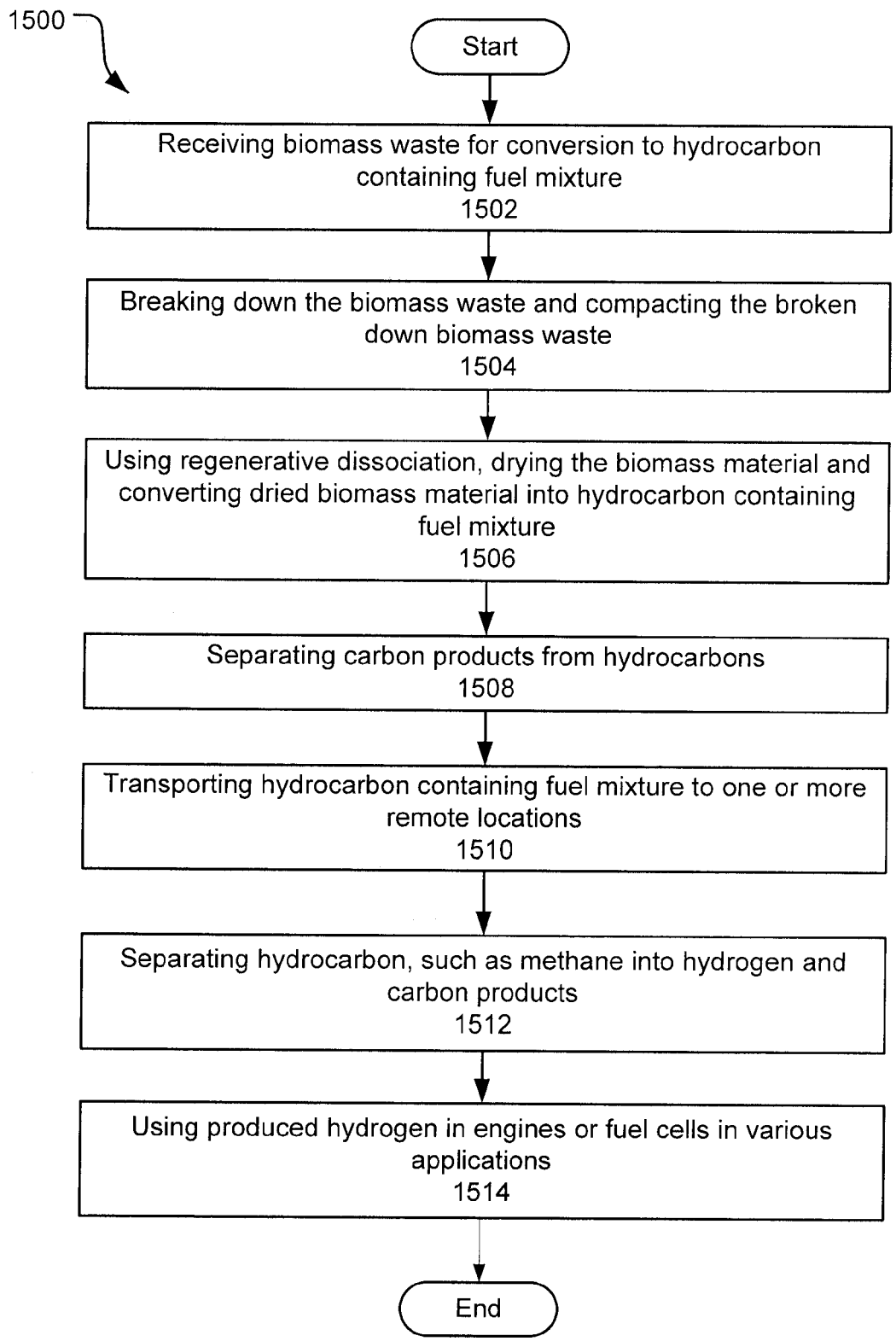
FIG. 15 is a process flow diagram showing a process for transporting renewable energy generated from biomass wastes, including municipal, farm, and forest wastes such as forest slash and diseased and/or dead trees.

A stationery base 1404 houses a drive system and provides transfer of materials to and from the reactor 1414. Fuels and feedstocks such as landfill methane for the reactor 1414 are delivered by a connected pipeline 1418. A fluid feedstock, such as sewage can be delivered to the reactor 1414 by a different pipeline 1415. Electricity produced or delivered is transferred by a cable group 1419. Hydrogen and/or other fluids produced by the reactor 1414 can be delivered to a pipeline 1416 for storage and distribution. A movable stage 1406 rotates around a central vertical axis to provide sun tracking of the reactor 1414 which is assembled with the mirror 1412. Coordinated rotation around a horizontal axis 1409 in support 1410 as shown is provided to track the sun and produce point focused solar energy reflected from the mirror assembly 1412. Organic solids and semisolids to be heated are loaded into a hopper 1408 which feeds organic solid materials into a screw conveyer 1424, a portion of which is shown in FIG. 15.

Other forms of renewable heating are readily adapted such as inductive or resistive heating using electricity from a generator powered by moving water, wind, wave action, or by an engine using fuel produced by the operation described herein. Similarly, a portion of the fuel produced by the reactor 1414 can be combusted to adequately heat zone 1430 for accomplishing the reactions of Equations 1, 4 and 6. This group of alternate heat inputs to the receiver zone 1430 illustrates means to supplement or replace solar energy as needed to assure continued operation in case of intermittent cloud cover or at night.

Supplemental heating or replacement of solar heat for zone 1430 by partial combustion of the produced hydrogen and/or carbon monoxide can be accomplished by delivering oxygen through tube 1437 within a bore 1431 of a tube 1432 from an electrolyzer 1407. A synergistic benefit is provided by the operation of a heat engine 1403 on the landfill methane and/or hydrogen for driving an electricity generator 1405. Surplus electricity generating capacity is used to produce oxygen and hydrogen in the electrolyzer 907. Hydrogen produced by such operation can readily be stored in a pipeline 1416 for transport and oxygen can be used to greatly improve the process efficiency of heat generation by partial combustion of the fuel produced by the reactor 1414 and/or in fuel cell power generation applications.

Elimination of nitrogen greatly reduces the cost of hydrogen purification by condensing or filtering water from the gas mixture within the tube 1432 when oxygen is used to produce heat by partial combustion. Tube 1437 delivers oxygen as shown to combust the amount of fuel needed with minimum heat loss and elimination of heating requirements for nitrogen which would be present if air is used as an oxidant.

Tube 1422 thus performs the functions of containing organic feedstocks in an anaerobic condition and transferring energy such as solar energy to the biomass conveyed into the concentrated heating zone 1430 to facilitate the reactions summarized as follows:

$$C_nH_mO_x + HEAT_1 \rightarrow xCO + m/2 H_2 + (n-x)C \qquad \text{Equation 12}$$

$$C_6H_{10}O_5 + HEAT_2 \rightarrow 5CO + 5H_2 + C \qquad \text{Equation 13}$$

Small amounts of $NH_3$, $H_2S$, $N_2$, and $H_2O$ may also be found in the gaseous products with the CO and $H_2$ that are forced by the compacted solids into the center bore 1431 of rotary screw tube 1432 as shown. The generated $H_2S$ can be reacted with iron to form iron sulfide or collected in carbon produced by the process as hydrogen is released. Fixed nitrogen can be collected as ammonia and sulfur as iron sulfide to be used as soil nutrients along with mineral ash collected.

Solids such as carbon and ash 1436 are extracted from the zone 1430 by the rotating motion of the screw tube 1432 along the flights 1434 as shown. High temperature insulation 1440 can be used to cover the end of the receiver/reactor 1414 as shown, and an insulated area 1442 can provide heat conservation along the countercurrent exchange of heat made between carbon rich solids being extracted by the screw conveyer 1432 and biomass moving towards the heated zone 1430 of the receiver and reactor assembly. During times that solar energy is not available, insulator sleeve 1438 is used to cover the zone 1430 and can be supported and guided to and from the stored position shown by telescoping tube guides, which are not shown.

Water and other gases removed at early stages of compaction and countercurrent pre-heating can be vented through louvers or holes 1444 to allow extraction through a collection tubes 1443 and 1446. For many feedstocks such as manure and sewage, this water generally contains fixed nitrogen and other soil nutrients and preferably is utilized to replenish soil tilth and productivity.

When pure carbon and pure hydrogen are preferred, the biomass may be pre-treated to remove ash forming materials such as calcium, magnesium, phosphorus, iron, and other minerals. Ash ingredients of biomass are often wastefully impounded in landfills or allowed to escape to the oceans as effluent is dumped from sewage and garbage disposal operations. In the described subject matter, ash is readily collected and returned to useful applications as a soil nutrient. This may be accomplished by a combination of mechanical separation and dissolution of the biomass in a suitable solvent to separate ash components.

Another embodiment provides anaerobic digestion of biomass such as carbohydrates and cellulose according to the following general reactions:

$$n(C_6H_{10}O_5) + nH_2O + HEAT_3 \rightarrow n(C_6H_{12}O_6) \qquad \text{Equation 14}$$

$$n(C_6H_{12}O_6) \rightarrow 3n(CH_4) + 3nCO_2 + HEAT_{10} \qquad \text{Equation 15}$$

Soil nutrients captured in the aqueous liquor remaining after the processes shown are efficiently transferred to depleted soils by various techniques including addition to irrigation water. Carbon dioxide is readily removed from the products of the process by cooling to produce phase change separation or by adsorption in a suitable solvent such as water. Carbon dioxide is soluble in water to the extent of about 21.6 volumes of gas per volume of water at 25 atmospheres pressure and 12° C. (54° F.).

Increasing the pressure and/or decreasing the temperature increases the amount of carbon dioxide dissolved per volume of water. After separation of carbon dioxide from methane, lowering the pressure or increasing the temperature releases dissolved carbon dioxide.

The amount of heat required in the process of anaerobic dissociation of organic feedstocks to produce a given amount of sequestered carbon is considerably less than the energy required to collect and dissociate carbon dioxide from the atmosphere. The apparatus required to practice the process of carbon sequestration from organic feedstocks is far less involved and much simpler and more rugged than would be required to extract carbon dioxide from the atmosphere and to break it into carbon and oxygen.

In the process of converting hydrocarbons including biomass solids and methane into carbon and hydrogen, the products of dissociation reactions tend to occupy more volume than the reactants. Apparatus 1420 of the assembly 1414 for carrying out these endothermic reactions can readily seal the reaction zone 1430 with carbon rich material that is compacted by extruder flights 1426 along the inlet to the reaction zone 1430 and with carbon rich material along extruder flights 1434 of the outlet of zone 1430 so that the hydrogen and other gases passing out through the bore 1431 may be pressurized to the desired extent and maintained by a rotary union and pressure regulation means on the outlet of the bore 1431.

Cool methane can be pressurized to the desired delivery pressure of hydrogen from the reactor 1420 with a suitable pressurization technique including pressurization by release from adsorptive substrates, phase change, mechanical compression, and hybridized systems before methane entry into reactor 1420. If the gases produced in anaerobic digestion are separated by liquefaction, this is readily accomplished by vaporizing the methane to the pressure desired. Pressurization by various pumps and compressors 1234 as shown in FIG. 12 may also be used for this purpose.

Types of carbon produced can vary based on market demand and the corresponding temperature and pressure at which the process of carbon sequestration is accomplished. For example, methane may be processed as needed to produce fibers, carbon black, diamond-like plating on suitable substrate, graphite crystals and in many other forms as described in U.S. Pat. Nos. 6,015,065 and 6,503,584.

Also, to provide heat conservation for certain applications, the screw conveyer 1432 can be designed as a feed path and a preheater with hydrogen being delivered through the bore 1431 and carbon produced by the reaction in zone 1430 conveyed by appropriately designed extruder 1424 in countercurrent heat exchange with the incoming feedstock. This arrangement can provide countercurrent heating of the incoming feedstock from the inside and from the outside before reaching the reaction zone 1430 by parallel flows of products passing in the opposite direction of feedstock.

Carbon formed by the reactor 1414 is carried by the screw conveyer 1432 in countercurrent heat exchange with the tube 1424 to preheat the incoming methane and thus increase the overall efficiency and rate that solar energy completes the process reactions. Hydrogen produced is collected in the bore 1431 of the tube conveyer 1432 and heat is removed in countercurrent heat exchange with reactants passing towards the reaction zone 1430.

Renewable hydrogen produced can be used in fuel cells or in heat engines that clean the air and provide cleaner exhaust than the ambient atmosphere.

Carbon continuously forms a gas-tight seal between the conveyer flights 1426 and the inner wall of the tube 1422 as it is produced by the process. This seal can be assured by reducing the helical extruder screw flight lead where the greatest compaction is desired. The greatest carbon compaction and sealing effect can be provided after the material undergoing conversion to hydrogen passes the reaction zone 1430 on the outlet in the screw conveyer past the reaction zone 1430.

Conveyance of reactants in the processes shown in FIGS. 14A and 14B can be performed by other analogous means in addition to the screw conveyers as shown. For example, the biomass could be forced to the reaction zone 1430 by a reciprocating plunger rather than the screw conveyer 1424 and carbon can be extracted from the hot end by other extraction methods including a chain drive conveyer rather than the screw conveyer 1432.

When producing a liquid fuel or vapors of a solvent such as one or more turpenes along with other valuable products, the reaction temperature may be adjusted to a reduced temperature or the throughput rate of the ingredients increased. Useful compounds such as hydrogen, carbon, methanol, biodiesel and turpentine may be produced and collected in the tube bore 1431 as summarized in the equations or a portion of a typical biomass waste feedstock with the average compound formula as shown below:

$$C_6H_{10}O_6 + HEAT_6 \rightarrow CH_3OH + 4CO + 3H_2 + C \qquad \text{Equation 16}$$

Incorporation of colloidal carbon that hosts adsorbed hydrogen in methanol provides higher heating value per volume and the ability to provide compression ignition in applications for renewable diesel fuel. If a greater yield of liquid fuel and/or solvent is desired, carbon monoxide and hydrogen produced in the typical process of Equation 16 may be reacted in the presence of a suitable catalyst to produce additional methanol and hydrogen.

$$4CO + 3H_2 \rightarrow 4CH_3OH + H_2 + HEAT_{12} \qquad \text{Equation 17}$$

The rate of biomass delivered into the reaction zone 1430 and the rate of extraction of solid residues by the helical conveyer 1432 can be controlled by a computer. For example, the computer can adaptively control the biomass conversion process in response to instrumentation of the pressure, temperature, and other indicators of the kind and quality of products desired in the gas, vapor and solid residue streams.

Carbon monoxide may be decomposed or converted to desired forms of sequestered carbon by disproportionation as shown by the process summarized in Equation 18:

$$2CO \rightarrow C + CO_2 + HEAT_{13} \qquad \text{Equation 18}$$

Disproportionation as summarized in Equation 18 is exothermic and can be provided under various combinations of temperature and pressure conditions including operations at 10-40 atmospheric pressure at 500° C. to 800° C.

For hydrogen production for fuel cells or heat engines that clean the air, carbon monoxide can be reacted with steam in an exothermic reaction to produce hydrogen as shown in Equation 19:

$$CO + H_2O \rightarrow CO_2 + H_2 + HEAT_{14} \qquad \text{Equation 19}$$

Carbon monoxide produced by the processes summarized above can be converted into numerous products to meet market demand as selected from processes requiring hydrogen and/or carbon production as illustrated. Heat released by the exothermic processes can be used as a part of the heat addition needed for endothermic reactions shown.

A practical process has been described for sequestration of carbon from the atmosphere using photosynthesis, collection of photosynthesized biomass, and heating the biomass to yield products selected from the group including carbon, hydrogen, methanol, turpenes, and ash. Biomass wastes that are ordinarily allowed to rot into the atmosphere and which contribute to carbon dioxide and/or methane buildup can now be utilized to efficiently produce hydrogen, carbon products and soil nutrients.

Tangible, Useful Applications

Analysis of fire, earthquake and mudslide hazards in most damaged forest settings show that it is highly advantageous to facilitate the solution presently disclosed by establishing underground pipelines to transport methane produced by rapid harvest and conversion of such damaged forests and/or groundcover. Pipeline shipment of such renewable methane to markets now served by natural gas or other fossil fuels can provide dramatic reductions in environmental impact from greenhouse gases and facilitate evolution from present dependence upon fossil energy to renewable energy security.

Also, job development and investor confidence can be bolstered by establishment of renewable sources of methane that can be delivered by low cost transport through pipelines. Further improvement can be provided by development of the "carbon age" that is facilitated by conversion of methane to carbon products as hydrogen is used for clean energy applications.

FIG. 15 is a process flow diagram showing a process 1500 for transporting renewable energy generated from biomass wastes, including municipal, farm, and forest wastes such as forest slash and diseased and/or dead trees. A biomass processing system (e.g., systems 200, 300, 600, 700, 800, 900 and 1100 described in FIGS. 2-3, 6-9 and 11 above) receives the biomass waste for conversion to renewable energy (process 1502). For example, the biomass waste from diseased and/or dead trees can be cut, pulled, or otherwise harvested. The biomass processing system chips or otherwise subdivides the harvested biomass wastes into bits and pieces for efficient transport and compaction by a conveyer such as a belt, ram, or screw conveyer (process 1504). Using regenerative dissociation, the biomass processing system dries and converts the subdivided biomass wastes to produce renewable energy and byproducts including hydrocarbons, alcohol vapors along with methane, hydrogen, and other gases along with solids such as carbon and minerals that are introduced by or along with the cellulose and/or lignocellulosic feedstocks (process 1506). The biomass processing system separates vapors and gases such as methane and or hydrogen from carbon dioxide (process 1508). The generated methane-rich gases can be shipped to remote locations by pipelines or other transport methods such as those utilized by the natural gas industry (step 1510). Hydrogen and carbon products can be produced from the methane-rich gases either before or after transporting the methane-rich gases through pipeline delivery (1512). The produced hydrogen can be used as fuel in various applications (1514). For example, hydrogen can be used in engines and/or fuel cells to power motor vehicles, to provide heat, for shaft work and electricity generation, for chemical process applications, and to produce fertilizers.

While this specification contains many specifics, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments.

Only a few implementations and examples are described and other implementations, enhancements and variations can be made based on what is described and illustrated in this application.

To the extent not previously incorporated herein by reference, the present application incorporates by reference in their entirety the subject matter of each of the following materials: U.S. patent application Ser. No. 12/857,553, filed on Aug. 16, 2010 and titled SUSTAINABLE ECONOMIC DEVELOPMENT THROUGH INTEGRATED PRODUCTION OF RENEWABLE ENERGY, MATERIALS RESOURCES, AND NUTRIENT REGIMES; U.S. patent application Ser. No. 12/857,553, filed on Aug. 16, 2010 and titled SYSTEMS AND METHODS FOR SUSTAINABLE ECONOMIC DEVELOPMENT THROUGH INTEGRATED FULL SPECTRUM PRODUCTION OF RENEWABLE ENERGY; U.S. patent application Ser. No. 12/857,554, filed on Aug. 16, 2010 and titled SYSTEMS AND METHODS FOR SUSTAINABLE ECONOMIC DEVELOPMENT THROUGH INTEGRATED FULL SPECTRUM PRODUCTION OF RENEWABLE MATERIAL RESOURCES USING SOLAR THERMAL; U.S. patent application Ser. No. 12/857,502, filed on Aug. 16, 2010 and titled ENERGY SYSTEM FOR DWELLING SUPPORT; U.S. patent application Ser. No. 13/027,235, filed on Feb. 14, 2011 and titled DELIVERY SYSTEMS WITH IN-LINE SELECTIVE EXTRACTION DEVICES AND ASSOCIATED METHODS OF OPERATION; U.S. Patent Application No. 61/401,699, filed on Aug. 16, 2010 and titled COMPREHENSIVE COST MODELING OF AUTOGENOUS SYSTEMS AND PROCESSES FOR THE PRODUCTION OF ENERGY, MATERIAL RESOURCES AND NUTRIENT REGIMES; U.S. patent application Ser. No. 13/027,208, filed on Feb. 14, 2011 and titled CHEMICAL PROCESSES AND REACTORS FOR EFFICIENTLY PRODUCING HYDROGEN FUELS AND STRUCTURAL MATERIALS, AND ASSOCIATED SYSTEMS AND METHODS; U.S. patent application Ser. No. 13/026,996, filed on Feb. 14, 2011 and titled REACTOR VESSELS WITH TRANSMISSIVE SURFACES FOR PRODUCING HYDROGEN-BASED FUELS AND STRUCTURAL ELEMENTS, AND ASSOCIATED SYSTEMS AND METHODS; U.S. patent application Ser. No. 13/027,015, filed on Feb. 14, 2011 and titled CHEMICAL REACTORS WITH RE-RADIATING SURFACES AND ASSOCIATED SYSTEMS AND METHODS; U.S. patent application Ser. No. 13/027,244, filed on Feb. 14, 2011 and titled THERMAL TRANSFER DEVICE AND ASSOCIATED SYSTEMS AND METHODS; U.S. patent application Ser. No. 13/026,990, filed on Feb. 14, 2011 and titled CHEMICAL REACTORS WITH ANNULARLY POSITIONED DELIVERY AND REMOVAL DEVICES, AND ASSOCIATED SYSTEMS AND METHODS; U.S. patent application Ser. No. 13/027,181, filed on Feb. 14, 2011 and titled REACTORS FOR CONDUCTING THERMOCHEMICAL PROCESSES WITH SOLAR HEAT INPUT, AND ASSOCIATED SYSTEMS AND METHODS; U.S. patent application Ser. No. 13/027,215, filed on Feb. 14, 2011 and titled INDUCTION FOR THERMOCHEMICAL PROCESS, AND ASSOCIATED SYSTEMS AND METHODS: U.S. patent application Ser. No. 13/027,198, filed on Feb. 14, 2011 and titled COUPLED THERMOCHEMICAL REACTORS AND ENGINES, AND ASSOCIATED SYSTEMS AND METHODS; U.S. Patent Application No. 61/385,508, filed on Sep. 22, 2010 and titled REDUCING AND HARVESTING DRAG ENERGY ON MOBILE ENGINES USING THERMAL CHEMICAL REGENERATION; U.S. patent application Ser. No. 13/027,060, filed on Feb. 14, 2011 and titled REACTOR VESSELS WITH PRESSURE AND HEAT TRANSFER FEATURES FOR PRODUCING HYDROGEN-BASED FUELS AND STRUCTURAL ELEMENTS, AND ASSOCIATED SYSTEMS AND METHODS; U.S. Patent Application No. 61/237,419, filed on Aug. 27, 2009 and titled CARBON SEQUESTRATION; U.S. patent application Ser. No. 13/027,196, filed on Feb. 14, 2011 and titled CARBON RECYCLING AND REINVESTMENT USING THERMOCHEMICAL REGENERATION: U.S. patent application Ser. No. 13/027,195, filed on Feb. 14, 2011 and titled OXYGENATED FUEL; U.S. Patent Application No. 61/237,425, filed on Aug. 27, 2009 and titled OXYGENATED FUEL PRODUCTION; U.S. patent application Ser. No. 13/027,197, filed on Feb. 14, 2011 and titled MULTI-PURPOSE RENEWABLE FUEL FOR ISOLATING CONTAMINANTS AND STORING ENERGY; U.S. Patent Application No. 61/421,189, filed on Dec. 8, 2010 and titled LIQUID FUELS FROM HYDROGEN, OXIDES OF CARBON, AND/OR NITROGEN; AND PRODUCTION OF CARBON FOR MANUFACTURING DURABLE GOODS; and U.S. patent application Ser. No. 13/027,185, filed on Feb. 14, 2011 and titled ENGINEERED FUEL STORAGE, RESPECIATION AND TRANSPORT.

What is claimed is:

1. A method for processing biomass wastes to produce a renewable fuel or a carbon byproduct or both, the method comprising:
   receiving a biomass waste that includes carbon, hydrogen and oxygen to be dissociated under an anaerobic reaction;
   recovering waste heat from an external heat source to heat the biomass waste, thereby removing air and moisture;
   compacting the biomass waste;
   advancing the compacted biomass waste in a dissociation zone;
   creating a seal from at least some of the advanced compacted biomass to seal off the dissociation zone; and
   applying heat to the advancing compacted biomass waste to create a pressure and temperature condition for dissociation of the biomass waste to produce the renewable fuel, the carbon byproduct, or both.

2. The method of claim 1, further comprising:
collecting the produced renewable fuel, carbon byproduct or both from the dissociation zone.

3. The method of claim 1, further comprising:
extracting other chemical species from the dissociation of the biomass in the dissociation zone.

4. The method of claim 3, wherein the extracted chemical species includes at least one of vaporous hydrocarbons, fuel alcohols, and gases such as ethane, methane, hydrogen, or oxides of carbon.

5. The method of claim 3, wherein the heat applied to the advancing compacted biomass waste is obtained via a countercurrent heat exchange from the extracted chemical species during cooling.

6. The method of claim 1, wherein recovering the waste heat comprises at least one of recovering heat rejected from an engine, or generating heat from a renewable energy generator including at least one of a wind energy generator, a solar energy generator, an energy generator from running water, or a geothermal energy generator.

7. The method of claim 1, wherein the renewable fuel comprises at least one of hydrocarbon, alcohol, ammonia, or hydrogen, and wherein the carbon byproduct comprises at least one of carbon dioxide, carbon monoxide, or carbon.

8. The method of claim 1, further comprising:
applying a catalyst to facilitate formation of the renewable energy comprising a hydrocarbon,
wherein the catalyst includes one or more of chromium, ceramics with rare earth constituents, a platinum metal group, nobleized nickel, and intermetallics of transition metals.

\* \* \* \* \*